United States Patent
Johnson et al.

(10) Patent No.: US 7,632,361 B2
(45) Date of Patent: Dec. 15, 2009

(54) SINGLE CRYSTAL SHAPE MEMORY ALLOY DEVICES AND METHODS

(75) Inventors: A. David Johnson, San Leandro, CA (US); Michael Bokaie, San Rafael, CA (US); Valery Martynov, San Francisco, CA (US)

(73) Assignee: TiNi Alloy Company, San Leandro, CA (US)

( * ) Notice: Subject to any disclaimer, the term of this patent is extended or adjusted under 35 U.S.C. 154(b) by 438 days.

(21) Appl. No.: 11/041,185

(22) Filed: Jan. 24, 2005

(65) Prior Publication Data

US 2009/0171294 A1 Jul. 2, 2009

Related U.S. Application Data

(60) Provisional application No. 60/569,659, filed on May 6, 2004.

(51) Int. Cl.
*C22C 9/01* (2006.01)
(52) U.S. Cl. .................. 148/402; 148/435; 623/1.19
(58) Field of Classification Search .......... 148/403, 148/435
See application file for complete search history.

(56) References Cited

U.S. PATENT DOCUMENTS

| | | |
|---|---|---|
| 368,425 A | 8/1887 | Ross et al. |
| 538,593 A | 4/1895 | Naylor, Jr. |
| 1,560,335 A | 11/1925 | Czochralski |
| 1,904,828 A | 4/1933 | Green |
| 1,926,925 A | 9/1933 | Wescott |
| 2,060,593 A | 11/1936 | Schaurte et al. |
| 2,371,614 A | 3/1945 | Graves |
| 2,586,556 A | 2/1952 | Mullikin |
| 2,608,996 A | 9/1952 | Forman |
| 2,610,300 A | 9/1952 | Walton et al. |
| 2,647,017 A | 7/1953 | Coulliette |
| 2,911,504 A | 11/1959 | Cohn |

(Continued)

FOREIGN PATENT DOCUMENTS

EP 0053596 6/1982

(Continued)

OTHER PUBLICATIONS

Article "Robototechnic Constructions Based On Cu-Al-Ni Single Crustal Actuators" by, I. E. Viahhi et. al. Published in Proceeding of the Second International Conference on Shape Memory and Superelastic Technologies in 1997.

(Continued)

*Primary Examiner*—George Wyszomierski
(74) *Attorney, Agent, or Firm*—Shay Glenn LLP

(57) ABSTRACT

Devices and methods of making devices having one or more components made of single crystal shape memory alloy capable of large recoverable distortions, defined herein as "hyperelastic" SMA. Recoverable Strains are as large as 9 percent, and in special circumstances as large as 22 percent. Hyperelastic SMAs exhibit no creep or gradual change during repeated cycling because there are no crystal boundaries. Hyperelastic properties are inherent in the single crystal as formed: no cold work or special heat treatment is necessary. Alloy components are Cu—Al—X where X may be Ni, Fe, Co, Mn. Single crystals are pulled from melt as in the Stepanov method and quenched by rapid cooling to prevent selective precipitation of individual elemental components. Conventional methods of finishing are used: milling, turning, electro-discharge machining, abrasion. Fields of application include aerospace, military, automotive, medical devices, microelectronics, and consumer products.

11 Claims, 10 Drawing Sheets

U.S. PATENT DOCUMENTS

| | | |
|---|---|---|
| 3,229,956 A | 1/1966 | White |
| 3,351,463 A | 11/1967 | Rozner et al. |
| 3,357,432 A | 12/1967 | Sparks |
| 3,400,906 A | 9/1968 | Stocklin |
| 3,408,890 A | 11/1968 | Bochman, Jr. |
| 3,445,086 A | 5/1969 | Quinn |
| 3,454,286 A | 7/1969 | Anderson et al. |
| 3,546,996 A | 12/1970 | Grijalva et al. |
| 3,561,537 A | 2/1971 | Dix et al. |
| 3,613,732 A | 10/1971 | Willson et al. |
| 3,620,212 A | 11/1971 | Fannon, Jr. et al. |
| 3,659,625 A | 5/1972 | Coiner et al. |
| 3,725,835 A | 4/1973 | Hopkins et al. |
| 3,789,838 A | 2/1974 | Fournier et al. |
| 3,849,756 A | 11/1974 | Hickling |
| 3,888,975 A | 6/1975 | Ramwell |
| 3,918,443 A | 11/1975 | Vennard et al. |
| 3,974,844 A | 8/1976 | Pimentel |
| 4,055,955 A | 11/1977 | Johnson |
| 4,063,831 A | 12/1977 | Meuret |
| 4,072,159 A | 2/1978 | Kurosawa |
| 4,096,993 A | 6/1978 | Behr |
| 4,176,719 A | 12/1979 | Bray |
| 4,177,327 A | 12/1979 | Mathews |
| 4,195,773 A | 4/1980 | Ogden |
| 4,243,963 A | 1/1981 | Jameel et al. |
| 4,265,684 A | 5/1981 | Boll |
| 4,279,790 A | 7/1981 | Nakajima |
| 4,340,049 A | 7/1982 | Munsch |
| 4,485,545 A | 12/1984 | Caverly |
| 4,501,058 A | 2/1985 | Schutzler |
| 4,524,343 A | 6/1985 | Morgan et al. |
| 4,549,717 A | 10/1985 | Dewaegheneire |
| 4,551,974 A | 11/1985 | Yaeger et al. |
| 4,553,393 A | 11/1985 | Ruoff |
| 4,558,715 A | 12/1985 | Walton et al. |
| 4,567,549 A | 1/1986 | Lemme |
| 4,585,209 A | 4/1986 | Aine et al. |
| 4,589,179 A | 5/1986 | Hulting, Jr. |
| 4,596,483 A | 6/1986 | Gabriel et al. |
| 4,619,284 A | 10/1986 | Delarue et al. |
| 4,654,191 A | 3/1987 | Krieg |
| 4,684,913 A | 8/1987 | Yaeger |
| 4,706,758 A | 11/1987 | Johnson |
| 4,753,465 A | 6/1988 | Dalby |
| 4,821,997 A | 4/1989 | Zdeblick |
| 4,823,607 A | 4/1989 | Howe et al. |
| 4,824,073 A | 4/1989 | Zdeblick |
| 4,848,388 A | 7/1989 | Waldbusser |
| 4,854,797 A | 8/1989 | Gourd |
| 4,864,824 A | 9/1989 | Gabriel et al. |
| 4,893,655 A | 1/1990 | Anderson |
| 4,896,728 A | 1/1990 | Wolff et al. |
| 4,915,773 A | 4/1990 | Kravetsky |
| 4,943,032 A | 7/1990 | Zdeblick |
| 5,060,888 A | 10/1991 | Vezain et al. |
| 5,061,137 A | 10/1991 | Gourd |
| 5,061,914 A | 10/1991 | Busch et al. |
| 5,069,419 A | 12/1991 | Jerman |
| 5,072,288 A | 12/1991 | MacDonald et al. |
| 5,114,504 A | 5/1992 | AbuJudom, II et al. |
| 5,116,252 A | 5/1992 | Hartman |
| 5,117,916 A | 6/1992 | Ohta et al. |
| 5,119,555 A | 6/1992 | Johnson |
| 5,129,753 A | 7/1992 | Wesley et al. |
| 5,160,233 A | 11/1992 | McKinnis |
| 5,190,546 A | 3/1993 | Jervis |
| 5,192,147 A | 3/1993 | McCloskey |
| 5,211,371 A | 5/1993 | Coffee |
| 5,218,998 A | 6/1993 | Bakken et al. |
| 5,245,738 A | 9/1993 | Johnson |
| 5,309,717 A | 5/1994 | Minch |
| 5,312,152 A | 5/1994 | Woebkenberg, Jr. et al. |
| 5,325,880 A | 7/1994 | Johnson et al. |
| 5,344,117 A | 9/1994 | Trah et al. |
| 5,364,046 A | 11/1994 | Dobbs et al. |
| 5,494,113 A | 2/1996 | Polan |
| 5,502,982 A | 4/1996 | Venetucci |
| 5,543,349 A | 8/1996 | Kurtz et al. |
| 5,605,543 A * | 2/1997 | Swanson ............... 604/102.02 |
| 5,619,177 A | 4/1997 | Johnson et al. |
| 5,622,225 A | 4/1997 | Sundholm |
| 5,640,217 A | 6/1997 | Hautcoeur et al. |
| 5,641,364 A | 6/1997 | Golberg et al. |
| 5,676,356 A | 10/1997 | Ekonen et al. |
| 5,695,504 A | 12/1997 | Gifford, III et al. |
| 5,714,690 A | 2/1998 | Burns et al. |
| 5,722,989 A | 3/1998 | Fitch et al. |
| 5,771,742 A | 6/1998 | Bokaie et al. |
| 5,772,378 A | 6/1998 | Keto-Tokoi |
| 5,796,152 A | 8/1998 | Carr et al. |
| 5,819,749 A | 10/1998 | Lee et al. |
| 5,825,275 A | 10/1998 | Wuttig et al. |
| 5,837,394 A | 11/1998 | Schumm, Jr. |
| 5,840,199 A | 11/1998 | Warren |
| 5,850,837 A * | 12/1998 | Shiroyama et al. .......... 128/892 |
| 5,867,302 A | 2/1999 | Fleming |
| 5,903,099 A | 5/1999 | Johnson et al. |
| 5,924,492 A | 7/1999 | Kikuchi et al. |
| 5,930,651 A | 7/1999 | Terasawa |
| 5,960,812 A | 10/1999 | Johnson |
| 6,042,553 A | 3/2000 | Solar et al. |
| 6,072,617 A | 6/2000 | Henck |
| 6,073,700 A | 6/2000 | Tsuji et al. |
| 6,075,239 A | 6/2000 | Aksyuk et al. |
| 6,080,160 A | 6/2000 | Chen |
| 6,084,849 A | 7/2000 | Durig et al. |
| 6,101,164 A | 8/2000 | Kado et al. |
| 6,110,204 A | 8/2000 | Lazarov et al. |
| 6,124,523 A | 9/2000 | Banas et al. |
| 6,126,371 A | 10/2000 | McCloskey |
| 6,139,143 A | 10/2000 | Brune et al. |
| 6,195,478 B1 | 2/2001 | Fouquet |
| 6,203,715 B1 | 3/2001 | Kim et al. |
| 6,229,640 B1 | 5/2001 | Zhang |
| 6,247,493 B1 | 6/2001 | Henderson |
| 6,277,133 B1 | 8/2001 | Kanesaka |
| 6,284,067 B1 | 9/2001 | Schwartz et al. |
| 6,386,507 B2 | 5/2002 | Dhuler et al. |
| 6,406,605 B1 | 6/2002 | Moles |
| 6,407,478 B1 | 6/2002 | Wood et al. |
| 6,410,360 B1 | 6/2002 | Steenberge |
| 6,447,478 B1 | 9/2002 | Maynard |
| 6,451,668 B1 | 9/2002 | Neumeier et al. |
| 6,454,913 B1 | 9/2002 | Rasmussen et al. |
| 6,470,108 B1 | 10/2002 | Johnson |
| 6,475,261 B1 | 11/2002 | Matsumoto et al. |
| 6,524,322 B1 | 2/2003 | Berreklouw |
| 6,533,905 B2 | 3/2003 | Johnson et al. |
| 6,537,310 B1 | 3/2003 | Palmaz et al. |
| 6,582,985 B2 | 6/2003 | Cabuz et al. |
| 6,592,724 B1 | 7/2003 | Rasmussen et al. |
| 6,605,111 B2 | 8/2003 | Bose et al. |
| 6,614,570 B2 | 9/2003 | Johnson et al. |
| 6,620,634 B2 | 9/2003 | Johnson et al. |
| 6,624,730 B2 | 9/2003 | Johnson et al. |
| 6,669,794 B1 | 12/2003 | Bellouard et al. |
| 6,669,795 B2 | 12/2003 | Johnson et al. |
| 6,672,502 B1 | 1/2004 | Paul et al. |
| 6,688,828 B1 | 2/2004 | Post |
| 6,729,599 B2 | 5/2004 | Johnson |
| 6,742,761 B2 | 6/2004 | Johnson et al. |
| 6,746,890 B2 | 6/2004 | Gupta et al. |
| 6,771,445 B1 | 8/2004 | Hamann et al. |

| | | |
|---|---|---|
| 6,790,298 B2 | 9/2004 | Johnson et al. |
| 6,811,910 B2 | 11/2004 | Tsai et al. |
| 6,840,329 B2 | 1/2005 | Kikuchi et al. |
| 6,843,465 B1 | 1/2005 | Scott |
| 6,908,275 B2 | 6/2005 | Nelson et al. |
| 6,920,966 B2 | 7/2005 | Buchele et al. |
| 6,955,187 B1 | 10/2005 | Johnson |
| 7,040,323 B1 | 5/2006 | Menchaca et al. |
| 7,044,596 B2 | 5/2006 | Park |
| 7,084,726 B2 | 8/2006 | Gupta et al. |
| 7,201,367 B2 | 4/2007 | Wietharn |
| 7,270,720 B2 * | 9/2007 | Brhel et al. .............. 148/562 |
| 2001/0023010 A1 | 9/2001 | Yamada et al. |
| 2002/0018325 A1 | 2/2002 | Nakatani et al. |
| 2002/0062154 A1 | 5/2002 | Ayers |
| 2003/0002994 A1 | 1/2003 | Johnson et al. |
| 2003/0078465 A1 | 4/2003 | Pai et al. |
| 2003/0170130 A1 | 9/2003 | Johnson |
| 2004/0083006 A1 | 4/2004 | Ellingsen |
| 2004/0200551 A1 * | 10/2004 | Brhel et al. .............. 148/562 |
| 2004/0243219 A1 * | 12/2004 | Fischer et al. ............ 623/1.15 |
| 2004/0249399 A1 | 12/2004 | Cinquin et al. |
| 2005/0113933 A1 | 5/2005 | Carter et al. |
| 2006/0118210 A1 | 6/2006 | Johnson |
| 2006/0213522 A1 | 9/2006 | Menchaca et al. |
| 2007/0137740 A1 | 6/2007 | Johnson et al. |
| 2007/0207321 A1 | 9/2007 | Abe et al. |
| 2007/0246233 A1 | 10/2007 | Johnson |

FOREIGN PATENT DOCUMENTS

| | | |
|---|---|---|
| EP | 0310439 | 4/1989 |
| EP | 1122526 | 8/2001 |
| EP | 1238600 A1 * | 9/2002 |
| GB | 2187951 | 9/1987 |
| JP | 57161031 | 10/1982 |
| JP | 59-179771 A * | 10/1984 |
| JP | 07090624 | 4/1995 |
| JP | 10173306 | 6/1998 |
| JP | 2000185999 A | 7/2000 |
| SU | 1434314 | 10/1988 |
| WO | WO 98/53362 | 11/1998 |
| WO | WO00/04204 | 1/2000 |
| WO | WO03/052150 | 6/2003 |
| WO | WO2005/108635 | 11/2005 |

OTHER PUBLICATIONS

Johnson, David et al.; U.S. Appl. No. 12/019,553 entitled "Frangible shape memory alloy fire sprinkler valve actuator," filed Jan. 24, 2008.
Johnson, David et al.; U.S. Appl. No. 10/972,745 entitled "Non-explosive releasable coupling device," filed Oct. 25, 2004.
Xiaogdang, Ma; U.S. Appl. No. 10/972,759 entitled "Magnetic data storage system," filed Oct. 25, 2004.
Johnson, David et al.; U.S. Appl. No. 11/006,501 entitled "Anastomosis device and method," filed Dec. 6, 2004.
Johnson, David; U.S. Appl. No. 11/396,234 entitled "Tear-resistant thin film methods of fabrication," filed Mar. 31, 2006.
Johnson, David; U.S. Appl. No. 11/415,885 entitled "Eyeglass frame," filed May 2, 2006.
Johnson, David; U.S. Appl. No. 11/420,157 entitled "Shape memory allow thin film, method of fabrication, and articles of manufacture," filed May 24, 2006.
Johnson, David; U.S. Appl. No. 11/526,138 entitled "Constant load bolt," filed Sep. 22, 2006.
Johnson, David; U.S. Appl. No. 11/859,697 entitled "Constant load fastener," filed Sep. 21, 2007.
Pauling, Linus, College Chemistry, second edition, W.H. Freeman and Company, San Francisco, 1955, pp. 81-91.
Buchaillot L. et al., "Thin film of titanium/nickel shape memory alloy for multi-degree of freedom microactuators", Seisan Kenkyu, vol. 51, No. 8, 1999, pp. 22-23.
Johnson A. D. et al., "Application of shape memory alloys: advantages, disadvantages, and limitations", Micromachining and Microfabrication Process Technology VII, 22-4 Oct. 2001, San Francisco, CA, USA, vol. 4557, 2001, pp. 341-351.
Takabayashi S. et al., "Reversible shape memory alloy film fabricated by RF sputtering", Materials and Manufacturing Processes, vol. 13, No. 2, 1998, pp. 275-286.
Martynov V., "TiNi thin films for microactuators and microdevices: sputter deposition and processing techniques", Thermec' 2003, International Conference on Processing and Manufacturing of Advanced Materials, Jul. 7-11, 2003, Leganes, Madrid, Spain, Materials Science Forum, vol. 426-432, Jul. 7, 2003, pp. 34.
Johnson, David et al.; U.S. Appl. No. 11/948,852 entitled "Method of alloying reactive elemental components," filed Nov. 30, 2007.
Johnson, David et al.; U.S. Appl. No. 11/949,663 entitled "Hyperelastic shape setting devices and fabrication methods," filed Dec. 3, 2007.
Antonov et al.; New advances and developments in the Stepnakov method for the growth of shaped crystals; Crystallography Reports; vol. 47; Suppl. 1; 2002; pp. S43-S52.
Creuziger et al.; Initial transformation around a notch tip in CuAlNi: experiment and modeling; Acta Materialia; vol. 56; pp. 518-526; 2008.
ElastametTM brochure from New Discovery Metals; 2007.
ElastametTM website screen capture, accessed Jul. 23, 2008.
Fu et al.; The growth characteristics with a shape memory effect; J. Phys.: Condens. Matter; vol. 4; 1992; pp. 8303-8310.
Morgan; Medical shape memory alloy applications—the market and its products; Materials Science and engineering A 378; 2004; pp. 16-23.
Qingfu et al.; Stabilisation of martensite during training of Cu-Al-Ni single crystals; Journal de Physique IV; Collloqu C2; Supplement to the Journa de Physique III; vol. 5; Feb. 1995; pp. 181-186.
Recarte et al.; Influence of Al and Ni concentration on the martensitic transformation in Cu-Al-Ni shape-memory alloys; Metallurgical and MaterialsTransactions A; vol. 33A; Aug. 2002; pp. 2581-2591.
Sittner et al.; Stress induced martensitic transformations in tension/torsion of CuAlNi single crystal tube; Scripta Materialia; vol. 48; 2003; pp. 1153-1159.
Sutou et al.; Development of medical guide wire of Cu-Al-Mn-base superelastic alloy with functionally graded characteristics; Mater Res Part B: Appl Biomater; vol. 69B; 2004; pp. 64-69.
Yahia et al.; Bioperformance of shape memory alloy single crystals; Bio-Medical Materials and Engineering; vol. 16; 2006; pp. 101-118.
Zhang et al.; The variant selection criteria in single-crystal CuAlNi shape memory alloys; Smart Mater. Struct.; vol. 9; 2000; pp. 571-581.
Zhdanov et al.; Thermal stresses in tubes, produced from a melt by the Stepanov method, during their cooling; Journal of Engineering Physics and Thermophysics; vol. 68; No. 1; 1995; pp. 80-89.
Johnson, Alfred David; U.S. Appl. No. 12/182,119 entitled "Method and devices for preventing restenosis in cardiovascular stents," filed Jul. 29, 2008.
Johnson, Alfred David; U.S. Appl. No. 12/325,722 entitled "Biocompatible copper-based single-crystal shape memory alloys," filed Dec. 1, 2008.

* cited by examiner

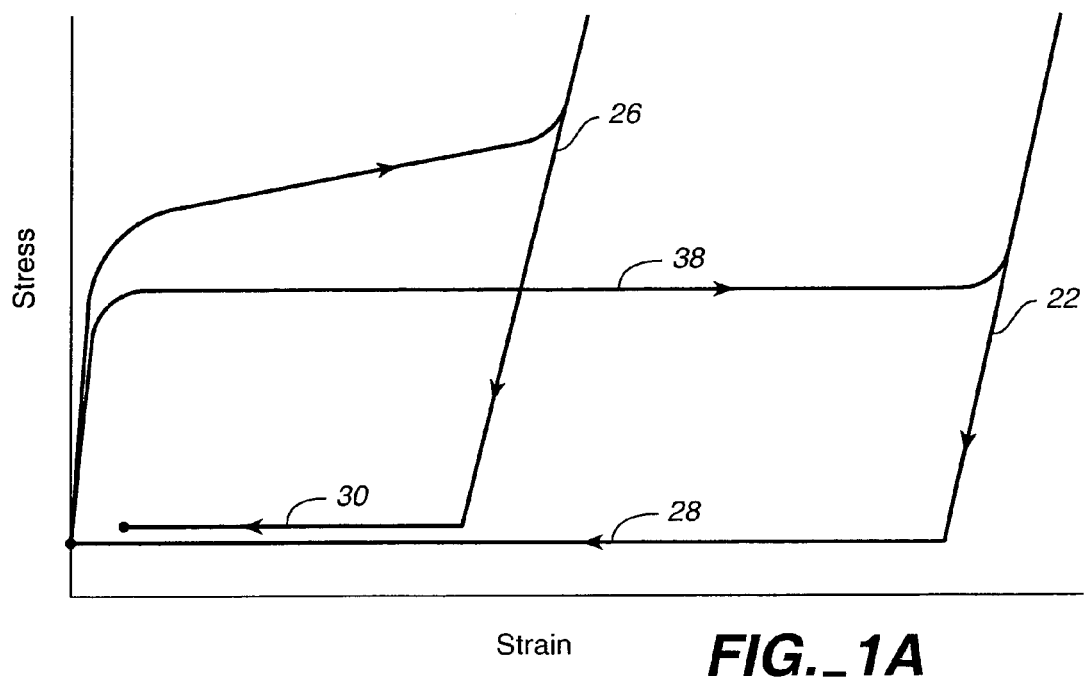
FIG._1A
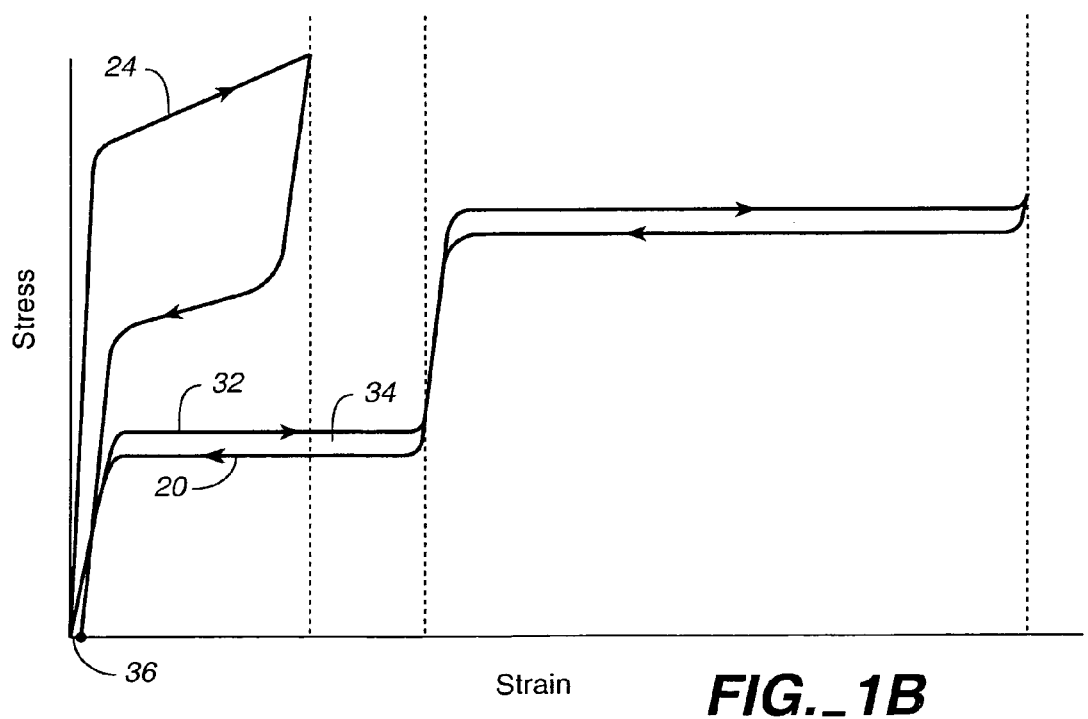
FIG._1B

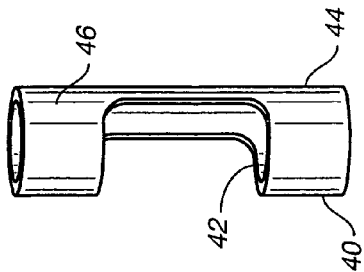
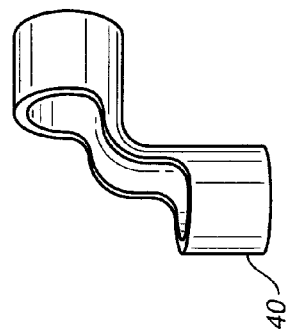
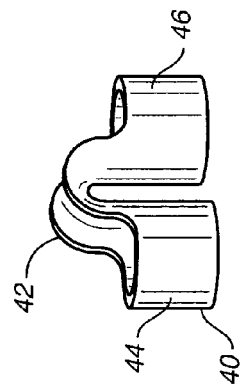
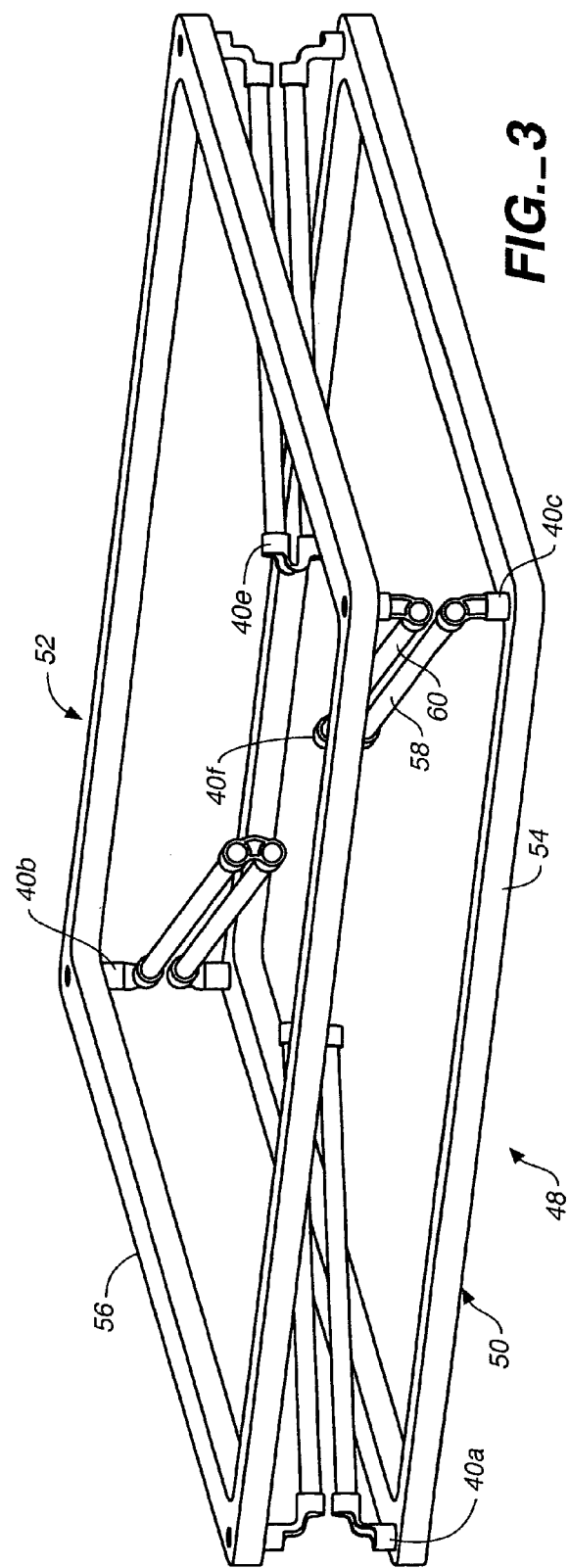

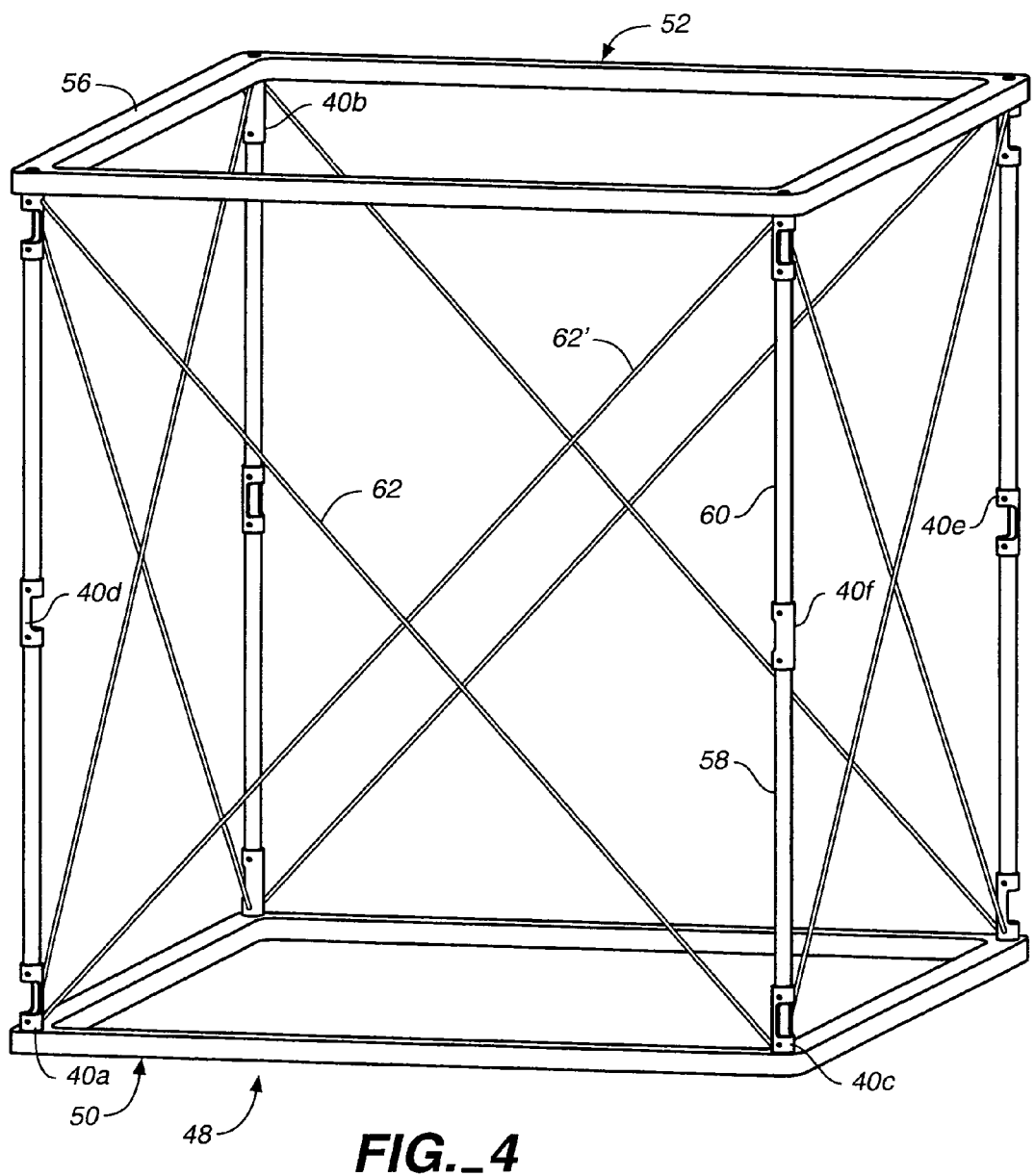
FIG._4

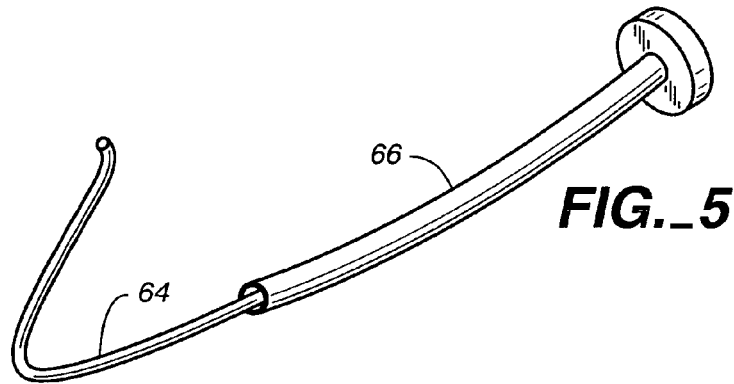
FIG._5
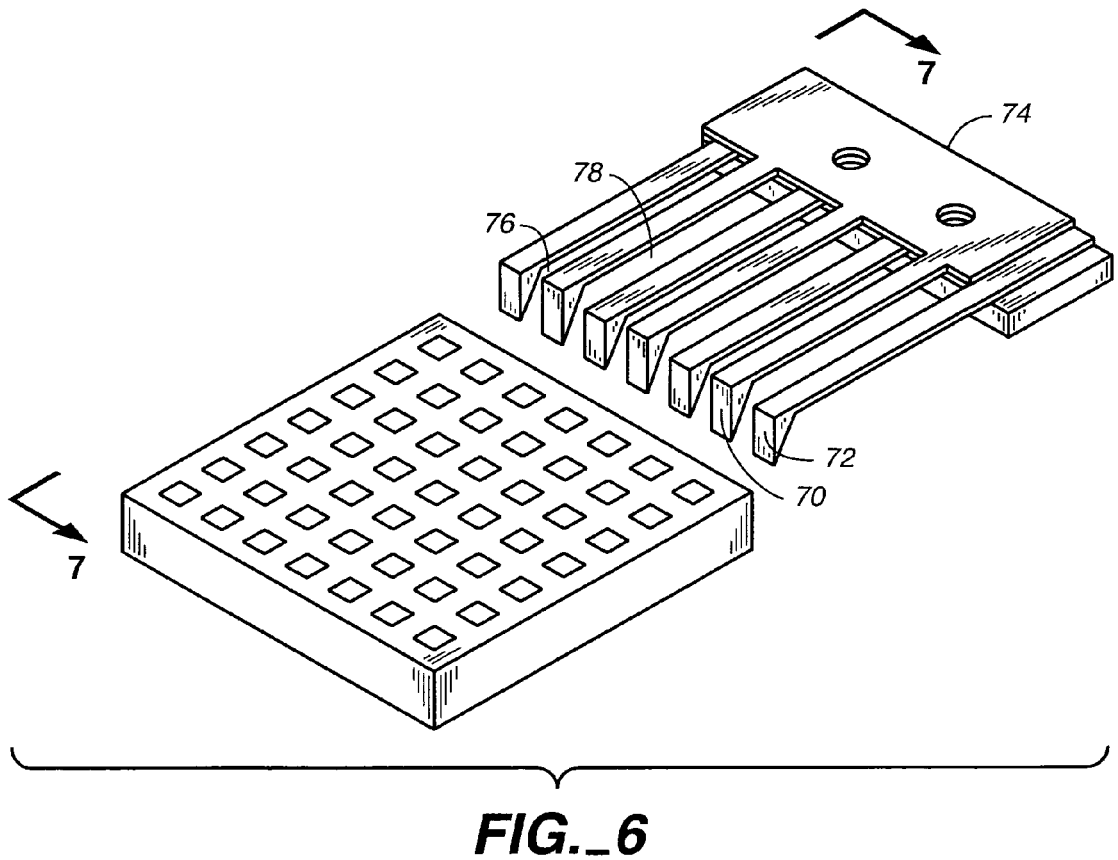
FIG._6
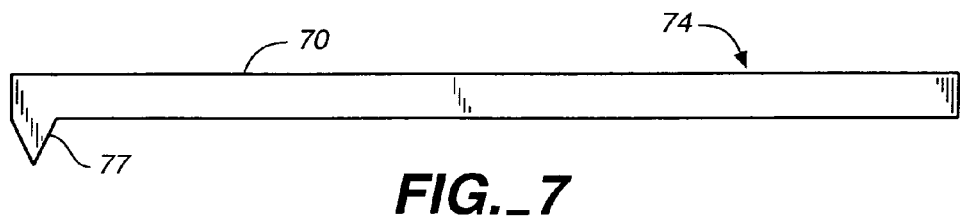
FIG._7

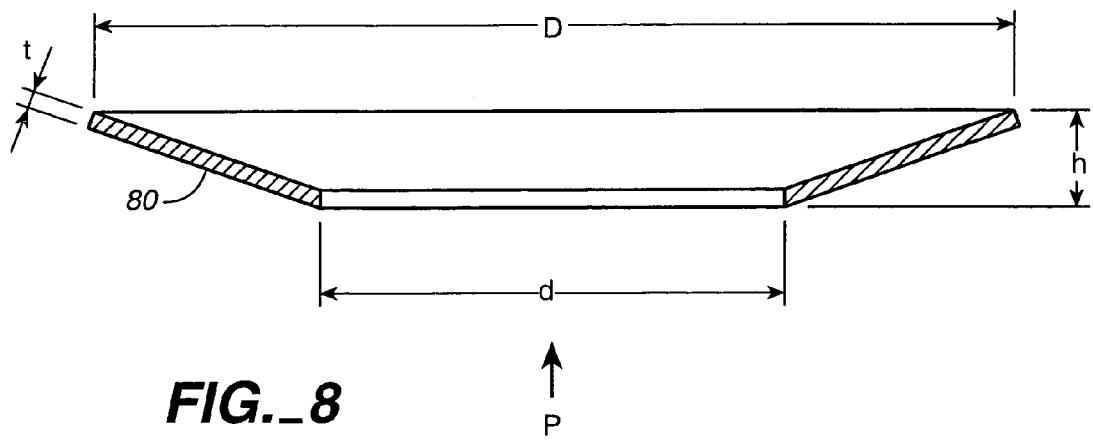
FIG._8
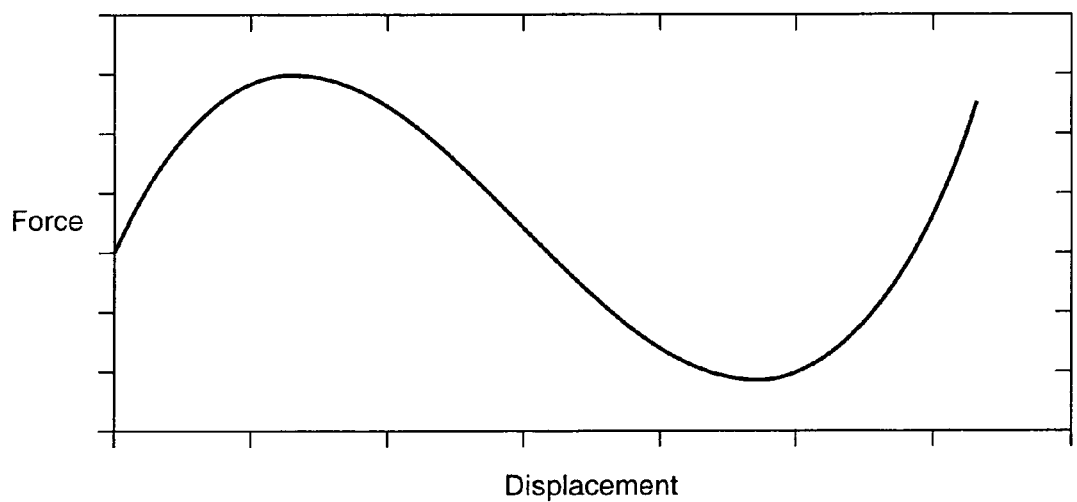
FIG._9

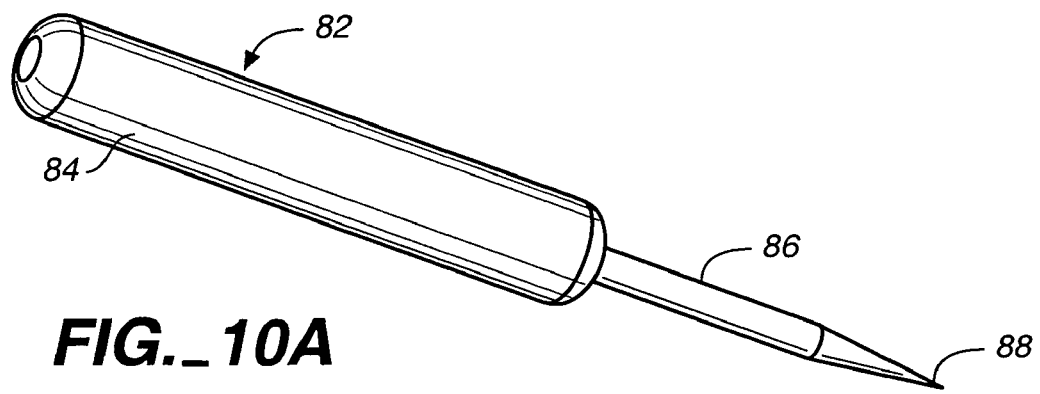
FIG._10A
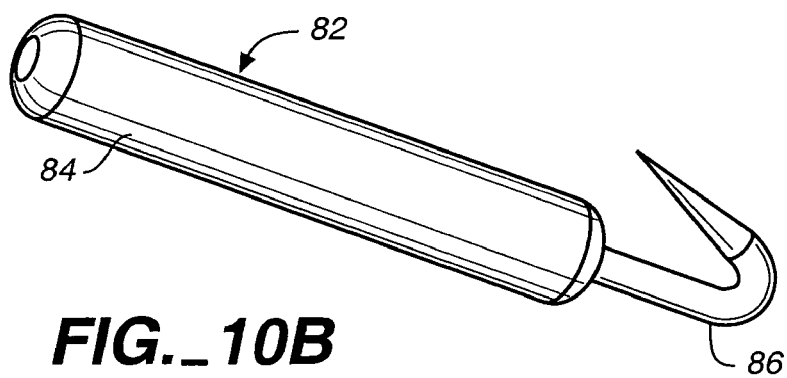
FIG._10B
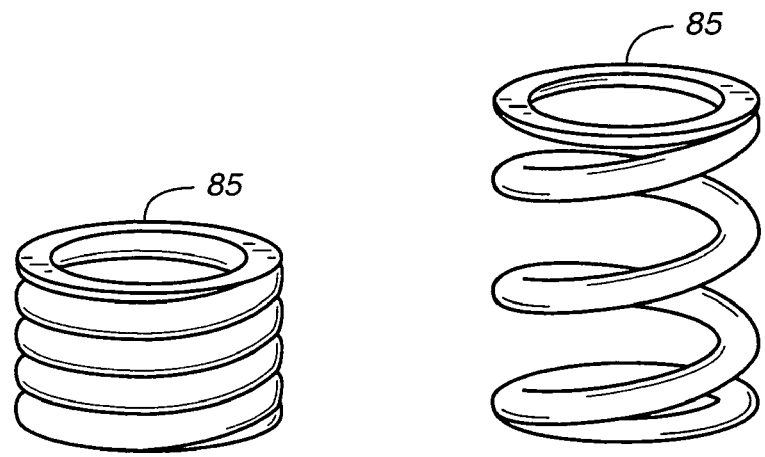
FIG._11A     FIG._11B

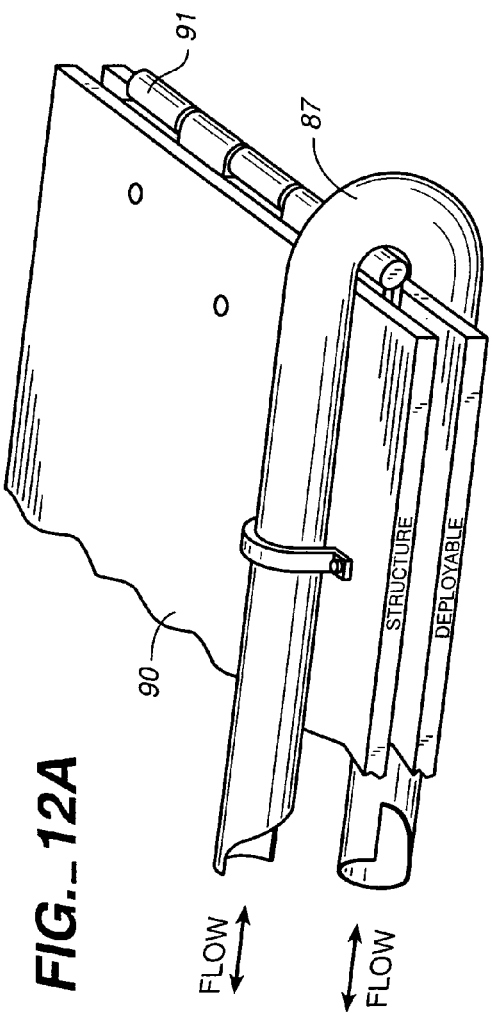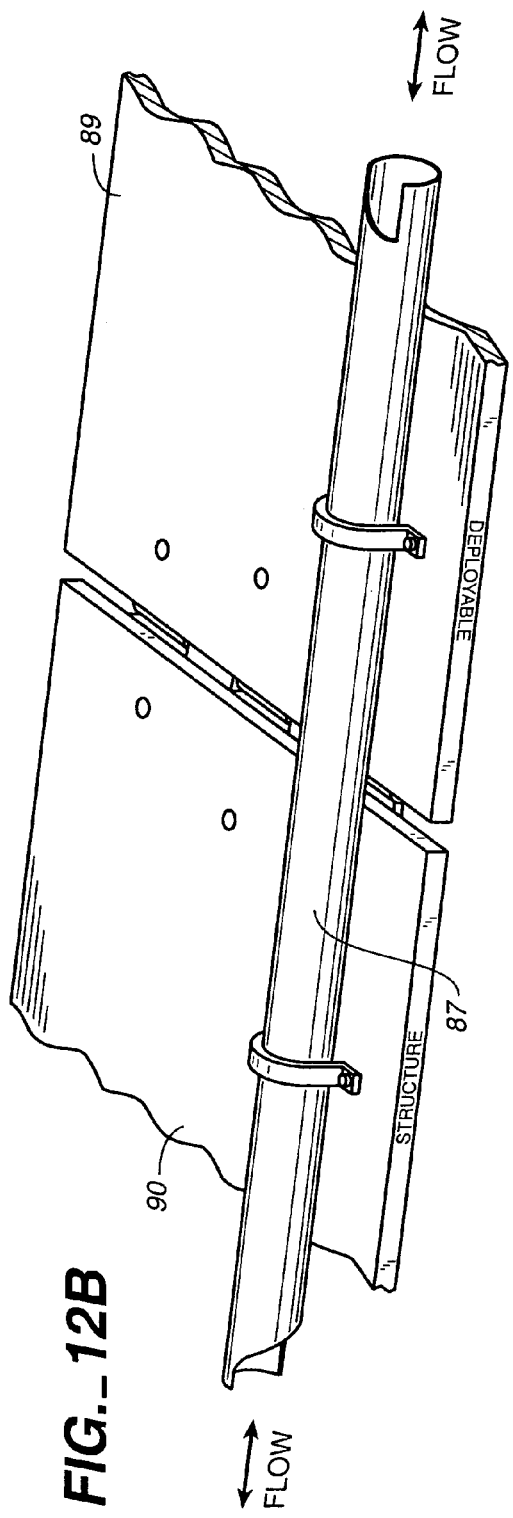

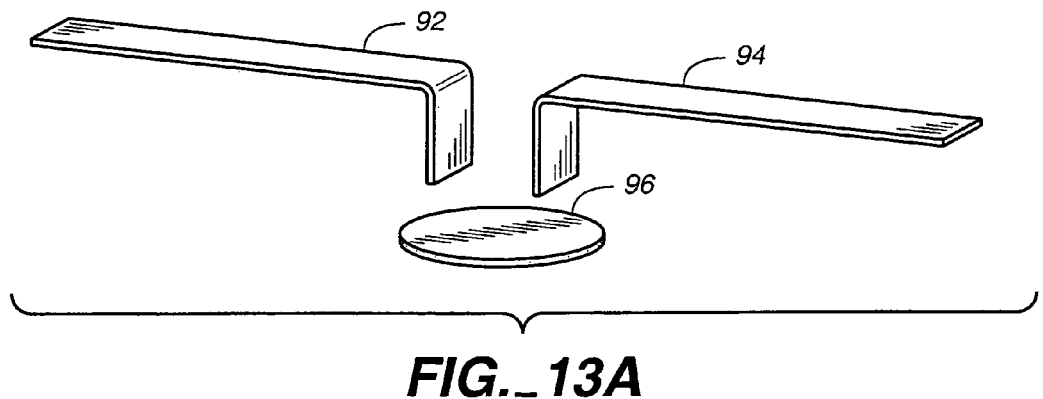
FIG._13A
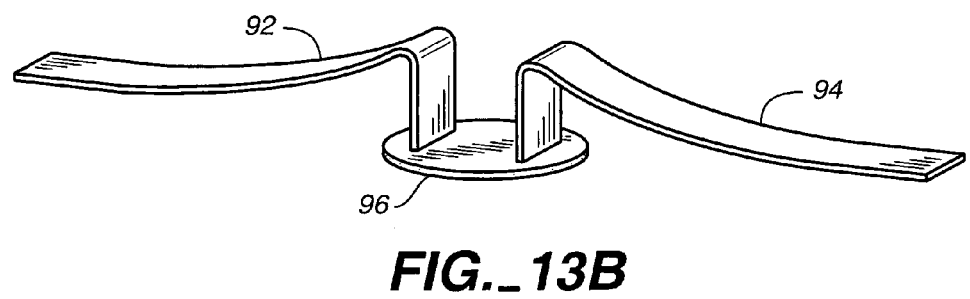
FIG._13B
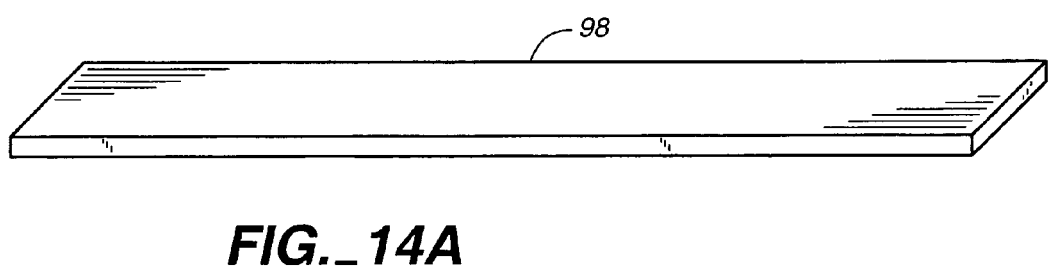
FIG._14A
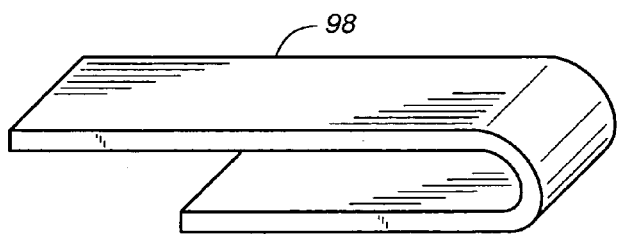
FIG._14B

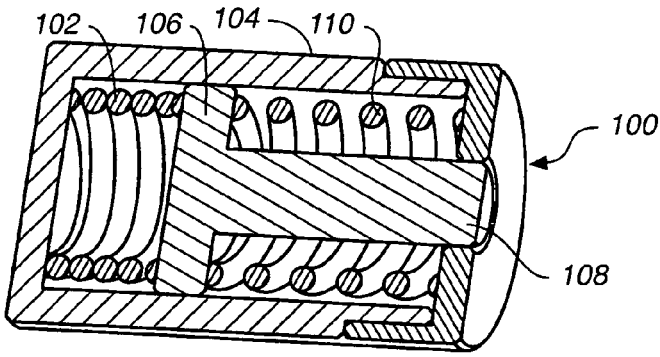
FIG._15A
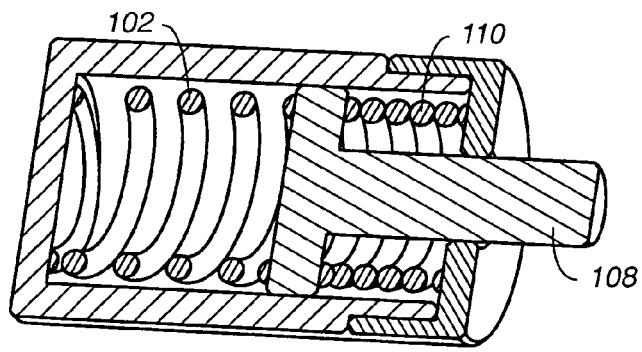
FIG._15B
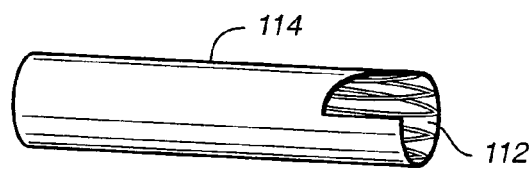
FIG._16A
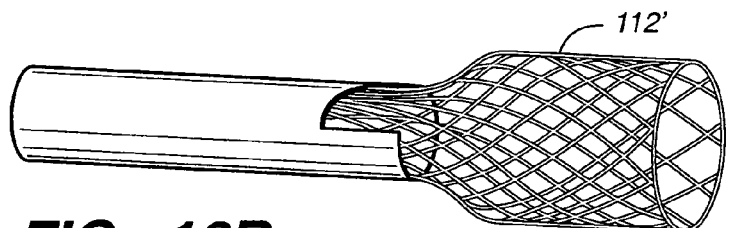
FIG._16B
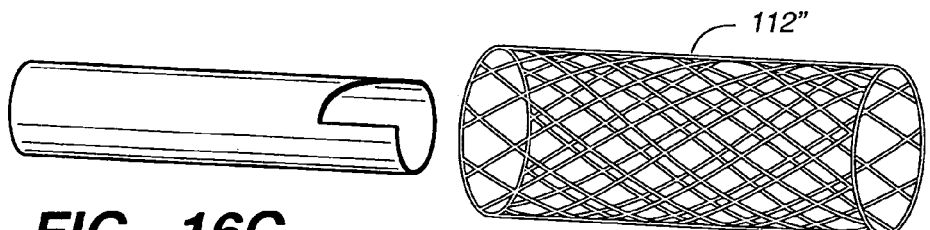
FIG._16C

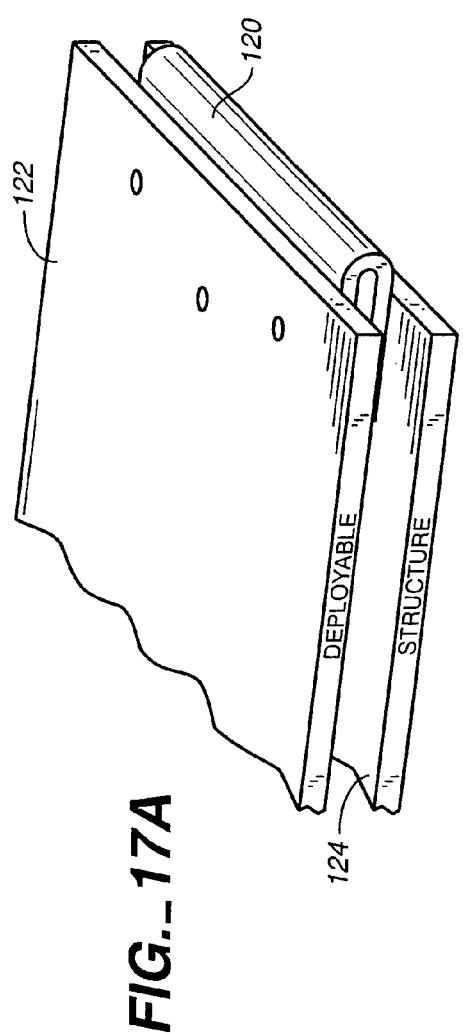
FIG._17A
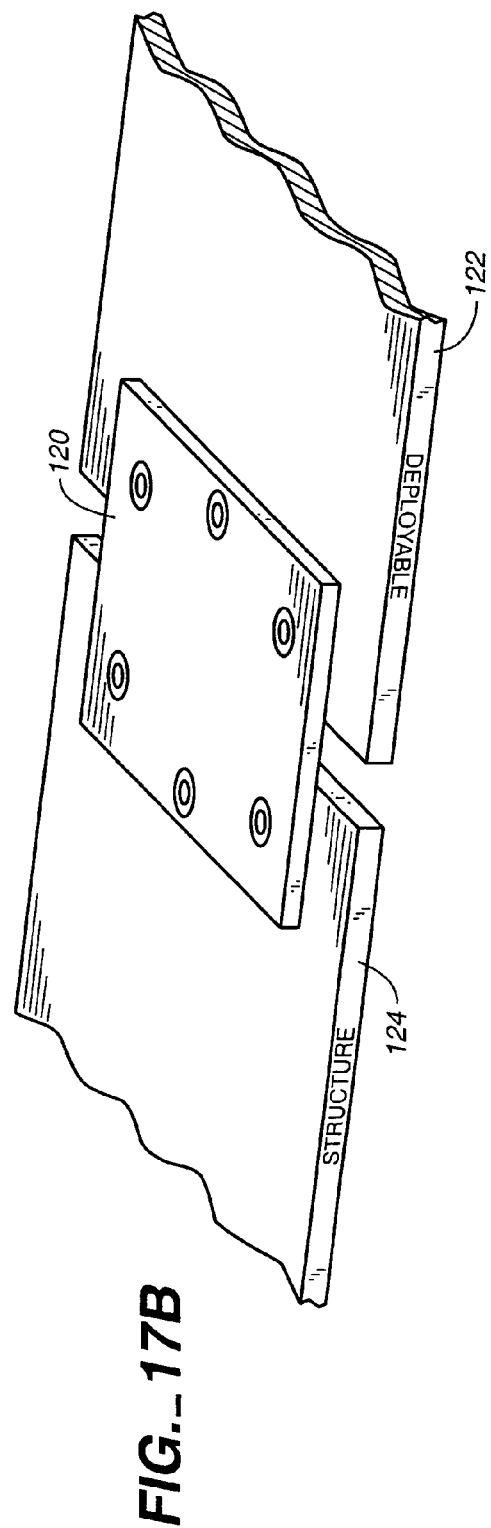
FIG._17B

SINGLE CRYSTAL SHAPE MEMORY ALLOY DEVICES AND METHODS

CROSS-REFERENCE TO PRIOR APPLICATION

This application claims the benefit under 35 USC §119(e) of U.S. provisional application Ser. No. 60/569,659 filed May 6, 2004.

BACKGROUND OF THE INVENTION

1. Field of the Invention

This invention relates to mechanical devices that have a component in which large recoverable distortions are advantageous.

2. Description of the Related Art

Shape memory alloy materials (also termed SMA) are well known. One Common SMA material is TiNi (also known as nitinol), which is an alloy of nearly equal atomic content of the elements Ti and Ni. Such an SMA material will undergo a crystalline phase transformation from martensite to austenite when heated through the material s phase change temperature. When below that temperature the material can be plastically deformed from a memory shape responsive to stress. When heated through the transformation temperature, it reverts to the memory shape while exerting considerable force.

In the prior art many different useful devices employing SMA have been developed and commercialized. The typical SMAs used in the prior art devices are of polycrystalline form. Polycrystalline SMA exhibits both: 1) shape memory recovery (when cycled through the material s transformation temperature) and 2) superelasticity. The term superelasticity applies to an SMA material which, when above the transformation temperature (in the austenite crystalline phase), exhibits a strain recovery of several percent. This is in comparison to a strain recovery on the order of only about 0.5 percent for non-SMA metals and metal alloys.

Superelasticity results from stress-induced conversion from austenite to martensite as stress is increased beyond a critical level, and reversion from martensite to austenite as stress is reduced below a second (lower) critical level. These phenomena produce a pair of plateaus of constant stress in the plot of stress versus strain at a particular temperature. Single crystal superelasticity is characterized by an abrupt change in slope of the stress strain plot at a combination of stress, strain, and temperature characteristic of that particular alloy.

Shape memory copper-aluminum based alloys grown as single crystals have been experimentally made in laboratories, typically in combination with about 5 percent Ni, Fe, Co, or Mn. The most common such CuAl-based alloy is CuAlNi, which is used throughout this description as the primary example: others are CuAlFe, CuAlCo, and CuAlMn. Single crystal SMA materials when stressed have the property of enabling a shape memory strain recovery much greater than polycrystalline SMA, and superelastic shape recovery as great as 24 percent.

BRIEF DESCRIPTION OF THE DRAWINGS

FIGS. 1A and 1B is a graph show the stress-strain curves for the typical superelastic properties of a polycrystalline SMA compared with the hyperelastic properties of single crystal SMA in accordance with the invention.

FIGS. 2A, 2B and 2C are perspective views of a snap-through hinge in accordance with another embodiment of the invention showing the hinge in different operating configurations.

FIG. 3 is a perspective view of an extendible boom in accordance with another embodiment incorporating the hinges of FIGS. 2A, 2B and 2C and in its stowed mode.

FIG. 4 is a perspective view of the extendible boom of FIG. 3 shown in its deployed mode.

FIG. 5 is a perspective view of a guidewire in accordance with another embodiment.

FIG. 6 is a perspective view of a group of probe tips in accordance with another embodiment.

FIG. 7 is a side view taken along the line 7-7 of FIG. 6.

FIG. 8 is an axial section view of a spring in accordance with another embodiment.

FIG. 9 is a load-deflection chart for the spring of FIG. 8.

FIGS. 10A and 10B are perspective views of a device useful as a probe or pin in accordance with another embodiment showing different operating positions.

FIGS. 11A and 11B are perspective views of a spring actuator in accordance with another embodiment showing different operating positions.

FIG. 12A is a perspective view of a heat pipe and deployable in accordance with another embodiment shown in one operating position.

FIG. 12B is a perspective view of the heat pipe and deployable of FIG. 12A shown in another operating position.

FIG. 13A is a perspective view of a switch flexure in accordance with another embodiment shown in one operating position.

FIG. 13B is a perspective view of the flexure of FIG. 13A shown in another operating position.

FIGS. 14A and 14B are perspective views of a leaf spring in accordance with another embodiment shown in different operating positions.

FIG. 15A is an axial section view of an actuator in accordance with another embodiment shown in one operating position.

FIG. 15B is an axial section view of the actuator of FIG. 15A shown in another operating position.

FIGS. 16A, 16B and 16C are perspective views of a collapsible tube in accordance with another embodiment shown in different operating positions.

FIG. 17A is a perspective view of a hinge for a deployable in accordance with another embodiment shown in one set of operating positions.

FIG. 17B is a perspective view of the hinge and deployable of FIG. 17A shown in another set of operating positions.

OBJECTS AND SUMMARY OF THE INVENTION

A general object of this invention is to provide new and improved devices and apparatus having a component or components in which large recoverable distortions can be advantageous.

The invention in summary provides devices and apparatus having at least one component made of a single crystal shape memory alloy, defined herein as hyperelastic SMA, having properties enabling the component to undergo large recoverable distortions. Such distortions can be at least an order of magnitude greater than that which could be obtained if the component were made of non-SMA metals and alloys, and nearly an order of magnitude greater than can be obtained with polycrystalline SMA materials. In different embodiments of the invention, devices and apparatus having components comprised of hyperelastic SMA can serve as: actuators for the active deployment of structures such as booms, antennae and solar panels; actuators for releasing door locks, moving mirrors and fuel injectors; flexures; constant force springs; connectors; dampeners; valves; microchip substrates; support members; non-explosive separation devices; catheter guide wires; laproscopic instruments; medical implants such as stents; micro-connectors; switches; circuit breakers; electronic test equipment; flexible electric cables; heat conductors; consumer products such as safety valves, eyeglass frames and cellular telephone antennae; and many other devices and apparatus in which large recoverable distortions of a component or components can be advantageous.

DESCRIPTION OF THE PREFERRED EMBODIMENTS

In its broadest concept, the present invention provides devices and apparatus having a component made of a single crystal SMA material which has the property of enabling a repeatable strain recovery of as much as 24 percent.

Because the range of strain recovery is so far beyond the maximum strain recovery of both conventional polycrystalline SMA materials and non-SMA metals and alloys, such repeatable strain recovery property of single crystal SMA is referred to herein as hyperelastic. Further, materials exhibiting hyperelastic properties are referred to herein as hyperelastic materials. Also as used herein, the phrase large recoverable distortion means the magnitude of repeatable strain recovery described above for a hyperelastic material.

Within the past two decades, SMA materials have become popular for use as actuators due to their ability to generate substantial stress during shape recovery of large strains during temperature-induced phase transformation. The energy density of such actuators is high compared to other alternatives, such as electromagnetic, electrostatic, bimetals, piezoelectric, and linear and volume thermal expansion effects of ordinary materials. The operating cycle of an SMA actuator includes deformation during or after cooling, and subsequent heating which results in a temperature-induced phase transformation and recovery of the deformation. SMA actuation is favored where relatively large force and small displacements are required in a device that is small in size and low in mass.

Shape memory is the ability of certain alloys to recover plastic deformation, which is based on a diffusionless solid-solid lattice distortive structural phase transformation. The performance of shape memory alloy based actuators strongly depends on the amount of recoverable deformation. In turn, recoverable deformation itself is a function of the lattice distortions which take place during martensitic phase transformation in the particular SMA. For an individual grain (single crystal) of SMA, the amount of possible recoverable strain after uniaxial loading, depends on the particular crystallographic orientation of the deformation tensor relative to the crystallographic axes of the high temperature (austenite) phase and the sign of applied load (tension or compression).

For a given deformation mode, the recoverable strain is strongly orientation dependent, and for the various crystallographic directions it differs by approximately a factor of two.

The recoverable deformation of these polycrystalline SMA alloys, due to the lattice distortion during diffusionless solid-solid phase transition, is substantially lower than is theoretically possible for a given material. The main reason for this is that for a conglomerate of randomly oriented grains (as is normally the case for polycrystalline materials), the average deformation will always be less than the maximum available value for a given grain. The diffusionless nature of phase transitions in SMA results in strict lattice correspondence between the high temperature (austenite) and low temperature (martensite) lattices. As the symmetry of the martensite lattice is lower than that of austenite, maximum deformation in each grain can only be attained in one particular crystallographic direction. This means that for randomly oriented grains (as normally is the case for polycrystalline materials), the average deformation will be at least a factor of two less than the maximum.

The restrictions imposed on a polycrystalline body by the deformation mechanism is another reason for diminished recoverable deformation in polycrystals as compared with a single crystal. To maintain integrity of the polycrystal, deformation of each particular grain has to be less than that corresponding to the theoretical limit for lattice distortion.

Therefore, for polycrystalline material, resultant recovery is the vector sum of particular grain deformations over the whole range of grain orientations, and is significantly smaller than the maximum value for an individual single crystalline grain.

By comparison, recoverable deformation close to the theoretical value (lattice distortion) can be achieved in single crystalline SMA. In addition to the substantially increased recoverable deformation, absence of grain boundaries results in increased strength and longer fatigue life. Specifically, as a single crystal, the strength of the grain for CuAlNi SMA can be as high as 800 MPa with the potential limit for recoverable deformation up to 9 percent and even higher for special deformation modes. An additional advantage of a single crystal SMA is that not only the thermally induced phase transformation may contribute to the recoverable deformation, as in the case for polycrystals, but also the stress-induced martensite-to-martensite phase transitions. Depending on the material, this additional contribution may be up to 15 percent; therefore the total theoretical recovery can be as high as 24 percent.

The graphs of FIGS. 1A and 1B show the stress-strain curves for a CuAlNi single crystal SMA of the invention as well for a prior art polycrystal TiNi SMA. Solid line curve 20 shows the single crystal SMA in its austenitic phase while curve 22 shows the martensitic phase. Solid line curve 24 shows the polycrystal SMA in its austenitic phase while curve 26 shows the martensitic phase. The graphs show the comparisons between the two SMAs as explained in the following.

The advantages of single crystal SMA over polycrystal SMA for mechanical devices include:

1. Greater than 9 percent strain recovery. In FIG. 1A the region 28 of curve 22 for the austenitic phase of the single hyperelastic SMA shows the magnitude of its strain recovery in comparison to the comparable region 30 of curve 26 for an austenitic polycrystal SMA. There is a three-fold gain in performance over the conventional SMA materials made from bulk materials, such as TiNi. Depending on how the sample is used, the greater than 9 percent recovery can either be used in the high temperature state (when in austenite phase) as a hyperelastic spring, for example, or deformed 9 percent (when in martensite phase) and then heated to recovery as an actuator.

2. True constant force deflection. Unlike polycrystalline materials which reach their strain/stress plateau strength in a gradual fashion and maintain an upward slope when deformed further, hyperelastic SMA materials have a very sharp and clear plateau strain/stress that provides a truly flat spring rate when deformed up to 9 percent. This is shown in FIG. 1B by the region 32 of curve 20. The stress level at which the plateau occurs depends on the temperature difference between the transformation temperature and the loading temperature.

Additionally, single crystal SMAs exhibiting hyperelasticity benefit from a second stress plateau which can increase the total recoverable strain to 22 percent.

3. Very narrow loading-unloading hysteresis. As a result there is substantially the same constant force spring rate during both loading (increasing stress) and unloading (decreasing stress). This is shown in FIG. 1B by the narrow vertical spacing 34 between the upper portion of curve 20 which represents loading and the lower portion representing unloading. This characteristic is key in applications where the flexure undergoes repeated cycling. In comparison, there is a relatively wide spacing between the corresponding loading and unloading portions of curve 24.

4. Recovery which is 100 percent repeatable and complete. One of the drawbacks of polycrystalline SMA materials has always been the "settling" that occurs as the material is cycled back and forth. This is shown in FIG. 1B for curve 24 by the spacing 36 of the curve end representing the beginning of the loading and the curve end representing the end of the unloading. The settling problem has required that the material be either "trained" as part of the manufacturing process, or designed into the application such that the permanent deformation which occurs over the first several cycles does not adversely affect the function of the device. By comparison, hyperelastic SMA materials do not develop such permanent deformations and therefore significantly simplify the design process into various applications. This is shown in FIG. 1B where the beginning of curve 20 representing unloading coincides with the end of the curve representing loading.

5. Very low yield strength when martensitic. This property is shown by the horizontal portion 38 of curve 22, which is relatively much lower than the corresponding portion of curve 26. The property is key for designing an SMA actuator which is two way (i.e., it cycles back and forth between two states). This is typically done by incorporating a biasing element, which overcomes the SMA when cold or martensitic, and establishes position one until the SMA is heated and overcomes the biasing element for driving the mechanism to position two. The problem with this type of device when using polycrystalline SMA is that the biasing element robs a significant amount of work output from the SMA. By comparison, an equivalent hyperelastic SMA element has a much lower yield strength when martensitic, enabling a much softer biasing element, and therefore generating a much greater net work output.

6. Ultra-low transition temperature. Hyperelastic SMA materials made from CuAlNi can be manufactured with transition temperatures close to absolute zero (−270 Celsius). This compares to SMA materials made from TiNi which have a practical transition temperature limit of −100 Celsius. The advantage from hyperelastic SMA is its use in various cryogenic applications such as those aboard spacecraft which require cooling of certain instruments and sensors to very cold temperatures. In this case a hyperelastic SMA actuator can be used as a valve to control flow of the cooling medium.

7. Intrinsic hyperelastic property. TiNi SMA can be conditioned, through a combination of alloying, heat treatment and cold working, to have superelastic properties. Single crystal CuAlNi SMA has intrinsic hyperelastic properties: a crystal of CuAlNi is hyperelastic immediately after being formed (pulled and quenched) with no further processing required.

Method of Fabricating Single Crystal SMA

Since single crystals cannot be processed by conventional hot or cold mechanical formation without breaking single crystallinity, a special procedure is required for shaping single crystals in the process of growth as the crystal is pulled from melt, resulting in finished shape.

Single crystal SMA is made in a special crystal-pulling apparatus. A seed of the desired alloy is lowered into a crucible containing a melted ingot of the alloy composition, and gradually drawn up. Surface tension pulls the melted metal along with the seed. The rising column cools as it leaves the surface of the melt. The rate of drawing is controlled to correspond with the rate of cooling so that a solid crystal is formed at a region that becomes a crystallization front. This front remains stationary while the crystal, liquid below and solid above, travels through it. The top surface of the melt can contain a die (of the desired cross-sectional shape) that forms the shape of the crystal as it grows. This procedure generally is known as the Stepanov method of making single crystals.

From the known Cu—Al phase diagram, rapid cooling (quenching) of the drawn crystal is necessary for production of single crystal beta phase that has the desired hyperelastic properties. Starting with beta phase at 850-1000 Celsius, if the alloy is cooled slowly the beta phase precipitates as beta+gamma, and at lower temperatures, as alpha+gamma-2. Single crystal beta phase, which requires that Al remains in solution at room temperature, is formed by rapid cooling in salt water from 850 Celsius. At elevated temperatures, above 300 Celsius, some decomposition gradually occurs; in fact, beta phase is not entirely stable at room temperatures but the time constant for decay is many years. The known phase diagram for the ternary CuAlNi alloy has similar characteristics.

General Description Of Device Applications Embodying The Invention

The various device applications contemplated by the invention with hyperelastic single crystal SMA are constrained by the intrinsic properties of the material, and by its behavior during forming and machining and other secondary manufacturing processes. For example, it has been shown that exposure to high temperature and/or stress can lead to recrystallization and the formation of unwanted crystals. The known forming and machining processes which are successful include lathe machining, electro-discharge machining (EDM), grinding, laser cutting, electro-polishing, and the like. These processes can be used to manufacture many basic shapes of the hyperelastic SMA, including rods, ribbons, flexures, coil springs, leaf springs, serrated tubes, tubes, pins and bi-stable elements.

Single crystal shape memory materials have significantly smaller thermal and mechanical hysteresis than polycrystalline materials. This is advantageous since less energy is absorbed in the material on each cycle, less heating occurs and more of the energy is recovered during the shape recovery.

Single crystal SMA hyperelastic components of mechanical devices generally provide a significant advantage over other device components currently available because they enable large displacement at constant force. For example, aerospace applications include actuators which may be used as motors to gently deploy spacecraft components such as booms, antennae and solar panels. Other aerospace applications include usage as constant force springs, flexures or connectors that need to accommodate very severe deformation but which spring back once the constraint is removed.

Commercial applications for hyperelastic SMA components are similarly of wide scope. They may be employed as a significantly improved replacement actuator or flexure over prior art SMA actuator applications. These applications include thermostatic valves, tools and instruments used in medicine, and other applications such as eyeglass frames and cellular telephone antennae.

The invention contemplates the following device applications having hyperelastic SMA components:

Aerospace and Military: As an actuator for active deployment of a host of devices including booms, antennae and solar panels.

As a flexure or constant force spring used for passive movement of cover doors or hinges.

As a connector where it is necessary to accommodate significant motion of adjacent parts. For example, heat pipes aboard spacecraft require such connectors to carry heating/cooling capability across a hinge to a deployable.

As a damper used to absorb or mitigate energy coming from nearby pyrotechnic release devices.

As a valve for a broad range of temperatures including cryogenic. Such valves have applications aboard missiles and satellites that carry sophisticated instruments such as sensors or cameras that need to be cryogenically cooled.

As an actuator in arming and safing ordnance.

As a substrate or support member for a surface or component which needs to accommodate large motion including applications on optical assemblies which require support and actuation (movement).

As a non-explosive separation device of smaller size than such bolts that are prior art.

As a flexible heat conductor or heat sink.

Medical:
For making catheter guidewires that are significantly more flexible than those currently made from stainless steel or polycrystal SMA. The CuAlNi alloy has no detectable cytotoxicity effect on the human body, and thus is compatible for use in a non-implantable function such as a catheter.

In laproscopic instruments where it is necessary to make tools which can tolerate large distortions.

In implants such as stents where the material can be made bio compatible by coating with Au.

Automotive: As an actuator for releasing door locks, moving mirrors and for driving fuel injector valves.

Computers
In micro-connectors and switches where large displacement capability allows for more reliable assembly, and for the fabrication of smaller parts.

Flexible cables for print-heads and the like.

Commercial:
As rings made for use as metallic connectors to secure braid in cabling applications.

Use in switches, relays, circuit breakers and electronic test equipment.

Consumer Products For use in safety valves, eye glass frames and automobile and cellular telephone antennae.

Embodiments Providing Equipment with Hyperelastic Components

The present embodiment provides the use of hyperelastic SMA in applications such as equipment for sports and other activities.

CuAlNi single crystal material stores an enormous amount of mechanical energy when it is deformed, and then releases the energy when the deforming force is removed. Unlike normally elastic material however the energy is stored and released at nearly constant force. These characteristics make this material desirable for use in equipment for use in a variety of sports and other activities including:

Bicycle wheel spokes equipped with a hyperelastic part to eliminate transmission to the hands of shocks due to small bumps in the road.

Running shoes and basketball shoes can contain a hyperelastic cushion that will reduce fatigue and enable the player to jump higher.

Skis that have a degree of hyperelastic behavior can reduce the shock of bumpy or irregular snow conditions and thereby improve control and provide a more comfortable, stable platform.

A warfighter may wear a form of 'exoskeleton' that enables a human to jump higher or survive descending from a higher distance than normal. The capacity for storage of mechanical energy is as much as 3 Joules gram of CuAlNi, and the majority of the energy is stored or released at a constant force resulting in constant acceleration. A parachutist, for example, wearing special boots containing a few hundred grams of CuAlNi would be protected from injury resulting from hitting the ground at a higher than usual speed.

Many of the above benefits will be most advantageous to amateurs, occasional athletes, and elderly people whose flexibility is impaired.

Snap-Through Hinge/Flexure Embodiments

The following embodiments provide devices such as hinges or flexures made of hyperelastic SMA that allow constrained relative motion without sliding or rotating components. These are used in space vehicles to provide lightweight structures such as booms that must be folded for launch into space. Similar flexures can also be used to replace prior art eyewear hinges.

These embodiments incorporate single-crystal hyperelastic materials into devices resembling tape-hinges resulting in superior load-carrying capability.

For spacecraft applications, the hinges/flexures must bend through an arc of 180 degrees to be useful in folding structures such as booms that are stored during launch in a minimal volume. Minimum size of the folded structure is achieved when the flexures bend through a minimal radius. In prior art implementations, flexures were made of thin steel curved tape. Steel in thin tape form does not provide optimum rigidity and strength for a functioning boom. This invention uses hyperelastic SMA in flexures capable of repeated recoverable large deformations to minimize size, maximize strength, and provide good vibration damping characteristics.

Among the design considerations for flexure design are that compression rigidity and resistance to buckling of the flexures should be consistent with that of the other components of the structure. These considerations set specifications for the flexure: length, thickness, width, curvature. This leads in turn to a design for a sliding die-mold for making the hyperelastic components.

In this embodiment, a tape hinge or flexure is formed by making a portion of a thin-walled cylinder and fixing it to rigid members or struts at the ends.

A principal feature of the invention is a "snap-through" action that resists bending because of its cylindrical symmetry which is very rigid for its mass, but when an applied force causes the flexure to buckle, it bends through a large angle with a smaller force. After buckling there is little restoring force because of its shape, that is, bending through a severe bending angle at a small radius of bend is possible because of the hyperelastic quality of the flexure. The flexure returns to its straight cylindrical rigid shape with a snap action because rigidity increases rapidly as the flexure assumes its cylindrical shell shape.

Performance of these devices, and their applicability, can be enhanced by increasing the recoverable strain, enlarging the stress tolerance, and extending the hyperelastic temperature range of the SMA materials. The method of deformation in tape-hinges results in non-uniform strain.

As the bending torque/moment is applied, the edge of the tape element is under tension, resulting in strain. After buckling occurs, this strain remains, and a bending moment is applied such that the inner surface is under compression and the outer surface is under tensile stress, with a neutral axis near the center of the cross-section.

Incorporating the SMA hyperelastic technology into a design in which all mechanical elements are in pure tension or pure compression, it becomes possible to build a structure that is very light, has a high packing factor for stowage, has a minimum of moving parts, and is very rigid for its weight. It is also possible to make it highly damped against vibrations. Hyperelastic alloys allow construction of structures that are strong against buckling while attaining a sharp radius of bend for compact folding.

It is desirable to make hinges that have no rotating or sliding parts. These devices can be used in spacecraft. One known form of hinge is a 'carpenter's tape' hinge. Such a hinge may be made by bending an elongate element having a thickness much smaller than the width and having a curved cross-section. Such an element has a 'snap-action'. These hinges when made of steel or materials with ordinary elasticity are restricted to a small thickness in order to control the degree of strain within the elastic limit of the material. Limiting the strain to elastic deformation limits the rigidity that can be achieved with BeCu and steel tape-spring hinges. Thus such prior art hinges are limited to relatively light loads, and Structures incorporating such hinges are not as rigid as is desired.

A material having greatly increased elasticity will enable the fabrication of 'carpenter's tape' hinges with increased load-carrying capacity. One such material is hyperelastic single-crystal copper aluminum nickel in accordance with the present invention. This embodiment provides a significant improvement in the performance of tape hinges by exploiting the properties of hyperelastic shape memory phase change material.

A material having greatly increased elasticity will enable the fabrication of 'carpenter's tape' hinges with increased load-carrying capacity.

FIGS. 2A, 2B and 2C illustrate different operational positions of a snap-through hinge or flexure 40 in accordance with one embodiment of the invention shown in FIG. 3. The flexure is comprised of a hollow tube of hyperelastic SMA. Between first and second flexure ends 44 and 46, the tube on one side is partially cut away to provide a weakened portion 42 that is in the shape of a circular segment in cross section.

As shown in FIG. 3, weakened portion 42 causes the flexure to undergo a snap-action or buckling action when its two ends are pivoted to a certain relative position (such as shown in FIG. 2B) between the stowed position with the shape of FIG. 2A and the deployed position with the shape of FIG. 2C. The FIG. 2B position is at the buckling point. The pivoting is initiated by a certain applied force until the buckling point is reached. Then mechanical energy stored in the flexure is released to continue the bending until the fully deployed position is reached. The full range of movement between the two positions is through an angle of 180 degrees or more.

Flexure 40 is adapted for use in coupling together components of the extendible boom segment 48 of FIGS. 3 and 4. Boom segment 48 has applications for use in spacecraft, such as for deploying payloads, positioning solar panels and the like. The boom segment comprises a pair of rigid frames 50, 52, each of which is comprised of four rigid side struts 54, 56 connected together at their ends to form a rectangular or square frame configuration. The four respective corners of the two frames are interconnected by four sets of paired longitudinal rigid struts 58, 60. When in the stowed position of FIG. 3 the longitudinal struts lay in planes that are parallel to the planes in which the frames lie. When in the deployed position of FIG. 4 each pair of longitudinal struts are coaxial and extend orthogonal with the planes of the frames. In the deployed position brace wires 62, 62 can be fitted diagonally between opposite corners of the squares or rectangles formed between the two frames.

A plurality (shown as eight for the two frames) of flexures 40a, couple together the outer ends of each pair of struts to respective corners of the two frames. One end of each such flexure is secured to the frame corner while the other end of that flexure is secured to the respective end of a strut. A plurality (shown as four for the two frames) of flexures 40d, couple together the inner ends of the strut pairs.

The flexures are operated toward their deployed positions by suitable actuators, not shown. For deployment, the actuators could be operated to move the two frames 50, 52 axially apart a distance sufficient to pivotally move the opposite ends of each flexure through arcs that cause the flexure to buckle and snap-through to the full 180 degrees arc of travel, which then becomes a stable position. A plurality of the boom segments could be mounted together in stacked relationship to form a boom structure that can deploy out to a longer overall length, as desired.

The snap-through hinge or flexure 40 offers additional stiffness when in the deployed position. In the prior art, hinge/flexure devices have been manufactured from materials such as Stainless Steel or Beryllium Copper. However, such devices aboard space applications have been limited to smaller deployables primarily because they lack the stiffness necessary to support larger structures. This is due to the very limited strain (<0.3 percent elastic) which these materials can endure. Therefore to achieve the necessary 180 degree fold for compact stowage, they must be made ultra thin reducing their axial stiffness. By comparison, the much greater strain recovery capability of hyperelastic SMA components allows flexures as in the present invention to be made on the order of 30 times thicker, providing an order of magnitude increase in axial rigidity.

Combining novel boom architecture with hyperelastic SMA enables implementation of ultralight, compact structures such as booms for use in space deployment of solar sails, large-aperture antennas, and optical instruments. These booms will have the advantages of light weight, minimal moving parts, and reduced stored mechanical energy compared to other folding structure designs.

Advantages and disadvantages of the hyperelastic tape hinge flexure/boom device embodiments of the invention include:

There are fewer moving parts. The flexure has only one part: it deploys by unfolding without sliding or rotating parts.

The boom can be scaled from a few cm to many meters in length. It has a potentially high packing factor; a large boom can be stowed in a small volume. Its deployed length to stowed length ratio may be 50 to one or higher.

Light weight. Since all elements are in pure tension or pure compression, it will be possible to optimize the elements for a particular design to minimize weight.

The boom contains no sliding or rotating parts. There is less opportunity for stiction to present a problem as may happen with age in a mechanism such as a hinge with a pin.

Each boom segment is readily re-stowable on the ground to permit testing. The segment could be made remotely re-stowable.

Hyperelastic Guidewire Embodiments

Guidewires are used to enable insertion of catheters into blood vessels and many other medical procedures. A guidewire is inserted ahead of the tip of the catheter, and then the catheter is advanced thought the blood vessel guided by the wire. The principal characteristics of guidewires are flexibility to permit following the contour of tortuous lumens, and resistance to kinking.

The best prior art guidewires in current use are superelastic wires made of polycrystalline SMA, principally TiNi. The superelastic property of TiNi limits the forces exerted by the wire against the blood vessel tissue while the wire bends as it follows curvatures of the lumen. TiNi superelastic guidewires are less susceptible to kinking than stainless steel wires, and they have good "torque-ability", that is they can be turned (twisted) along their long axis without objectionable flexing.

Single-crystal wires of CuAlNi SMA exhibit hyperelasticity compared to prior art shape memory wires, and the shape recovery is total rather than partial, as shown in FIG. 1. These properties are exploited to produce guidewires that can access blood vessels that are so tortuous as to be inaccessible or nearly inaccessible to prior art guidewires.

Method of Forming Hyperelastic SMA Wires

Rods of CuAlNi are formed by pulling them from a melted ingot by the Stepanov method. The composition of the ingot from which the wire is drawn can be adjusted, thereby lowering its transformation temperature, and making the wire stiffer. The composition of the ingot is made such that at human body temperature of 37 Celsius, the CuAlNi material is hyperelastic The rod is subsequently re-heated and quenched by rapid cooling to retain the nickel and aluminum dissolved in the copper matrix. The rod is heated in an air furnace and dropped into a salt-water bath. Salt water is used for the quenching bath because fewer bubbles are formed and the resulting temperature drop is more rapid.

CuAlNi single crystal material cannot be plastically deformed to reduced diameter, so after quenching the rod is centerless ground and otherwise processed by abrasive machining to achieve the desired size and shape. The rod may be processed by conventional machining so long as the surface stresses are not so great as to cause multiple large crystals to form at the surface. Micro- or nano-crystals may be removed by abrasion and polishing, including electro-polishing.

The rod may also be processed by EDM. After EDM, the surface should be abraded to remove the re-deposited material and micro- or nano-crystals that may have formed. Otherwise these may act as a source for crack initiation. Single crystal CuAlNi is notch and crack sensitive, making it appear brittle if the surface is not smooth.

Wires of single crystal CuAlNi SMA can be deformed more than TiNi wires and still recover all of the deformation without damage when the restraining force is removed. Increased flexibility enables a CuAlNi wire to bend through a smaller radius without becoming permanently deformed. Hence CuAlNi SMA guidewires are superior to those made of polycrystalline SMAs such as Nitinol.

In hyperelastic SMA wires stiffness is not isotropic. For example, a wire can be elongated in the <100> direction much more easily and to a larger strain than in the <110> direction. This is used to advantage for making guidewires that are very flexible but have good 'torque-ability'.

Stiffness can be tuned from wire to wire. Two wires of the same diameter may be designed to have different stiffness through minor adjustments in the composition.

Stiffness can also be tuned along the length of a wire by two methods. First, differing composition can be accomplished, as an ingot of a given composition can be used as a seed for pulling a second ingot as a continuous single crystal of slightly different composition having increased or diminished stiffness. Second, the fraction of aluminum that remains in solution depends on the temperature to which the material is heated before quenching. In that case, a heater is provided to heat one end of the wire to a slightly higher temperature than the other so that when the wire is quenched by rapid submersion in salt water the cooler end has less dissolved aluminum and nickel.

Description of a Guidewire Embodiment

FIG. 5 illustrates an embodiment of the invention, which comprises a hyperelastic guidewire 64 of single crystal SMA. The guidewire is shown with its distal end protruding from the forward end of a catheter 66, although the invention contemplates use of a hyperelastic guidewire in other procedures within the human body.

The guidewire is formed with a thickness in the range 0.012 to 0.039 inches, and preferably 0.018 and 0.038 inches. The guidewire can have different lengths depending on the application. The preferred length is in the range of 42 and 100 inches.

The hyperelastic SMA guidewire can be fabricated with a non-elastic segment, such as the tip. This is accomplished by making the segment of single crystal SMA having a transition temperature above body temperature of 37° C. The material in this segment is then martensitic, is easily deformed, and remains deformed after being deformed. Deformation can be removed by heating to above the transformation temperature while the object is at zero external stress so that the wire can be inserted into a lumen. At the desired position within the lumen, the segment is then heated by suitable means above the transition temperature so that the tip reverts to its memory shape with the specific curve or turn and in which the tip segment remains non-elastic as long as it is above the transition temperature.

CuAlNi can also be combined with other materials to make composite materials with specific properties. CuAlNi single crystal can be pulled from melt as a cylinder or tube. Adding lubricants can increase tube lubricity. The single crystal CuAlNi wires can be coated with polymers or with metals. Such coatings can be used for providing increased biocompatibility.

Single Crystal SMA Guidewire Advantages

The advantages of the guidewires of the invention include their suitability for use in minimally invasive surgery, especially intravascular procedures. The guidewires have increased flexibility compared with conventional materials used in such procedures. The guidewires enable surgeons of ordinary skill to perform certain specific procedures that currently require highly skilled specialists. The guidewires of these embodiments can save time in the operating room. The guidewires have the ability to be more versatile than ordinary prior art guidewires, in particular enabling the surgeon to use the same guidewire both for entering a tortuous lumen and for deployment of a balloon or other appliance.

Probe Tip Embodiments

Microelectronics circuits, fabricated on silicon dies, are becoming smaller, more complex, and faster. Each of these characteristics raises problems with manufacture.

The microelectronics industry faces two principal problems: extreme miniaturization and high data transfer rates, which manifests itself as High frequencies. The time may be approaching when microelectronics circuits on chips can be manufactured but cannot be adequately tested during manufacture.

Smaller chips mean that spacing between contact pads becomes smaller. Typical pitch of bonding pads ('bumps') is now smaller than 0.5 mm. Recommended contact force is in the tens of grams.

Increasing complexity brings with it a need for increased testing during manufacture. Wafers, dies, and die modules are tested before installation of a component in a system. This increased testing is expensive: up to 60 percent of manufacturing cost. And increased handling can lead to damage of the die unless the contacts are carefully probed. Each test runs some risk of damage to the die, so that methods that minimize damage are desirable to optimize yield.

Microprocessors now operate at multiple gigahertz rates. At such high frequencies, radiation from exposed conductors as short as a few millimeters is significant, leading to cross talk between connectors and loss of signal strength. A method of shielding leads, analogous to coaxial cable, would ameliorate this source of testing failure.

A solution to these problems is constrained by requirements of manufacturing:

Every new tool should be backwards compatible so that new equipment can be integrated with existing equipment and methods.

Methods should not damage pads.

Contact should have 'wipe' to remove oxide and make low-ohmic contact.

Contact force should be adequate for low-ohmic contact: tens of grams.

Compliance is needed to compensate for tolerances in pad height and misalignment of dies in fixturing.

Variation in height of 'bumps' is of the order of 0.0001 to 0.001 inches. 2.5 to 25 micrometers)

A method of contact that is reversible (that is, a temporary contact in the sense that it can be un-made) would solve many problems. Soldered contacts are not easily reversed, and damage is likely. Differential thermal expansion of silicon dies and ball grid arrays means that re-flowed solder is deformed repeatedly throughout the lifetime as the chip is heated and cooled. Solder hardens and crystallizes with time, and becomes brittle. When it fractures, malfunctions (especially intermittent problems) occur.

The present embodiment provides means of establishing temporary low-resistance electrical connections with greatly increased compliance and uniform contacting force. For this purpose an alloy with high electrical conductivity and hyperelasticity is used: single crystal copper-aluminum-nickel SMA. Such an alloy constitutes an enabling technology for surmounting the problems of electrical connectors in microelectronics manufacture and testing.

Single crystal CuAlNi may be deformed (strained) more than 9 percent, and recovery is complete. After a linear elastic region, the typical stress-strain isothermal curve for hyperelastic CuAlNi is a plateau. Recovery produces a second plateau. Hysteresis is minimal. Fatigue lifetime is many millions of cycles. Component materials are inexpensive, and low cost may be achieved in mass manufacture. Electrical resistivity is low.

Among the advantages that electrical contacts made from hyperelastic CuAlNi provide over existing tungsten and molybdenum needles are:

Hyperelastic contacts that produce the same force regardless of displacement means that the total force for a specific number of contacts is constant and predictable.

Good electrical conductance (low resistivity) means less loss of power and less generation of heat.

Enablement of systems for reversible electrical contact directly to the bare die or bumps on the bare die. Such a system would enable multi-chip modules to be reversibly assembled, and if one chip in a module fails, it may be replaced rather than discard the entire module or attempt to un-solder it for repair.

The potential to provide small, low-ohmic, reversible, minimally-damaging, constant-force electrical contactors for die testing and for assembly of die modules.

Electrical contactors made of single-crystal CuAlNi are capable of large strain; their mode of deformation is hyperelastic; repeated large strains are completely recovered with no fatigue.

Method of Fabricating Single-Crystal CuAlNi Probe Tips.

Single crystal rods of CuAlNi are pulled from melted ingot by the Stepanov method, then heated and quenched to lock in the dissolved aluminum.

From the phase diagram for Cu—Al it may be seen that quenching is necessary to retain dissolved Al. When the alloy is cooled slowly the beta phase precipitates as beta+gamma, and at lower temperatures, as alpha+gamma-2. Beta phase has desirable hyperelastic qualities. A similar phase diagram applies to the ternary CuAlNi system.

Individual needles of CuAlNi are cut from rods and formed to shape by conventional methods of machining, including electrical discharge machining and sawing (dicing). After machining operations the individual components are smoothed to remove surface micro-cracks and nano-crystals that are formed on the surface by heat and/or stress. Smoothing may be done by abrasives or by electropolishing.

Description of Probe Tip Embodiment

FIGS. 6 and 7 illustrate certain of the steps in fabricating a plurality of probe tips 70, 72 in accordance with the invention. A round single crystal boule 5 mm-10 mm diameter is pulled from CuAlNi melt. The boule is heated to 900 Celsius and quenched in salt water. A thin rectangular parallelepiped slice 74 (0.01 to 0.1 mm thick, 2 to 10 mm wide, and 8 to 15 mm long) is cut from the boule by the EDM process. At the same time, a plurality (shown as six) of spaced-apart slots 76, 78 are cut at one end of the slice to define seven cantilevers, 70, 72 between the slots. The slice is cut to have the shape of FIG. 6 along the <100> direction of the crystal. As the slots are formed a wedge shaped feature or point 77 is formed on the end of each cantilever to define a row of sharp points. The slots are cut very narrow parallel to the <100> direction. The cantilevers are typically 3 mm long and spaced apart a distance of 0.1 to 0.5 mm. Narrow slots, not shown, are formed as extensions from slots 76, 78 to mechanically separate and electrically isolate the individual cantilevers.

The assembly comprising the cantilevers on slice 74 is then affixed to a PC board, not shown, carrying traces that make electrical contacts with the cantilevers.

Large Displacement Spring Embodiment

The present embodiment comprises a spring, shown at 80 in FIG. 8, of the well-known Belleville washer configuration and which is comprised of a hyperelastic CuAlNi SMA material.

Belleville washers are used in applications that require storage of a large amount of energy in a small volume. Materials used for Belleville washers include steel, beryllium copper, and stainless steel.

FIG. 9 illustrates the force-displacement curve for a Belleville spring made of hardened stainless steel. This type of spring is very stiff unless it is extremely thin, and the stroke is necessarily small or the steel becomes overstrained. Use of hyperelastic SMA enables a much larger stroke.

The present embodiment of a Belleville washer configuration formed of hyperelastic CuAlNi SMA provides for springs with extremely different characteristics from those made of ordinary materials. The shape of the force-displacement curve for materials with ordinary elasticity is dictated by the Young's modulus E which, for normally elastic elements, is constant. In the case of hyperelastic materials, E is constant up to the 'knee' of the stress-strain curve, beyond which point the force is nearly constant as the stress-strain curve becomes a plateau: Young's modulus E becomes a dependent variable. In the case of a Belleville spring the stress varies along a radius, so the point at which E changes depends on position. This non-linear behavior of a hyperelastic alloy makes calculation or simulation of behavior by calculation difficult and unproductive. Instead, devices are fabricated and force versus distance characteristics are measured in trial and error fashion.

Bistable Element Embodiments

Bistable elements such as buckling beams and Belleville washers made from Hyperelastic SMA have improved characteristics compared to bistable elements fabricated from ordinary materials such as steel and beryllium copper. In particular, the sidewise displacement of a buckling beam of specific dimensions can be an order of magnitude larger than that of a beam of material with ordinary elasticity, and the force needed to change the state of a bistable buckling beam is much less. This permits their use in miniature switches and valves.

A buckling element uses material in pure compressive stress or in bending which is a combination of compression and tension. Hyperelastic CuAlNi has different characteristics in compression than in tension. This enables designs that are not feasible with normal materials. Because the modulus for compression is higher than the modulus for tensile stress the neutral axis does not correspond to the geometrical center of a bending beam.

Embodiments Providing Probes and Pins

FIGS. 10A and 10B show an embodiment comprising a device 82 for use as a probe, such as for medical use in the human body, or as a pin for releasably securing things together, or as a needle. Device 82 is comprised of a proximal end 84, which can be a handle or catheter, and a distal end 86 formed with a pointed tip 88. The distal end is formed of a hyperelastic CuAlNi SMA. FIG. 10A shows the distal end in its low temperature martensite state, while FIG. 10B shows the distal end it its high temperature austenite state, which is its "memory" shape. In the illustrated embodiment the memory shape is in the form of a hook. The use of hyperelastic CuAlNi SMA in place of other materials such as superelastic TiNi SMA provides advantages comprising allowing for more severe bending of the distal end, and greater resistance to breakage or other failures.

Embodiment Providing Spring Actuator

FIGS. 11A and 11B show an embodiment comprising a compression coil spring 85, which can be used as an actuator. Spring 85 is formed of a hyperelastic SMA. FIG. 11A shows the spring in its low temperature martensite state. FIG. 11B shows the distal end it its high temperature austenite state, which is its "memory" shape. In the illustrated embodiment the memory shape is where the coils axially expand to apply a force, such as to throw a switch or the like. Other hyperelastic SMA spring configurations, such as those which apply tension or which apply torsion when in their memory shapes, are within the scope of the invention.

Embodiment Providing Bendable Heat Pipe

FIGS. 12A and 12B show an embodiment comprising a heat pipe 87. The heat pipe is formed of a hyperelastic single CuAlNi SMA. With the pipe formed of this material, it can tolerate severe bending without failure. It is shown adapted for use on a spacecraft having a deployable 89 (only a part of which is shown) which is pivotally connected by a hinge 91 with a structure or frame 90. A gas or liquid is directed by the pipe across the hinge line, such as for use on the deployable. The hyperelastic properties enable bending of the pipe through a wide arc of travel, shown as 180 degrees. FIG. 12A shows the pipe in a bent shape with the deployable stowed. FIG. 12B shows the pipe bent to a straight shape after the deployable is pivoted out into its deployed position.

Embodiment Providing Flexures for Electrical Switches

FIGS. 13A and 13B show an embodiment comprising a pair of hyperelastic flexures 92, 94, such as for use in a small size electrical switch having a moving contact 96 for opening and closing a circuit. Each flexure is formed of a hyperelastic CuAlNi SMA. The hyperelastic properties enable the flexures and contact to be very small while allowing the flexures to easily yield by bending upon upward movement of the contact. This allows the switch to be more forgiving (and therefore more reliable in its operation) of any variations in switch part dimensions due to manufacturing tolerances. FIG. 13A shows the parts before the flexures are touched by the contact so that the circuit is open. FIG. 13B shows the flexures after being touched by and yieldably bent by the contact to close the circuit.

Embodiment Providing Leaf Spring

FIGS. 14A and 14B show an embodiment comprising a leaf spring 98. The spring is formed of a hyperelastic SMA. The hyperelastic properties enable extreme bending of the spring. As a result, the spring is optimum for use in aerospace applications where size and mass must be minimized. FIG. 14A shows the spring before bending. FIG. 14B shows the spring after being bent through a wide arc, illustrated as 180 degrees.

The constant force plateau of stress resulting from the hyperelastic properties also provides significant advantages in giving the spring an inherent "snap-action" feature. Further, the hyperelastic properties minimize the total energy stored when fully bent (i.e. strained up to its failure point).

Embodiment Providing Plunger Actuator

FIGS. 15A and 15B show an embodiment comprising a plunger type actuator 100. The actuator is comprised of a main spring 102, shown as a coil spring although it could be in other configurations, mounted coaxially within a cylindrical shell housing 104. Spring 102 is formed of a hyperelastic SMA. A plunger 106 is slidably mounted within the housing so that elongation of the main spring drives the plunger's distal end 108 out through the end of the housing. A bias coil spring 110 is mounted within the housing on a side of the plunger opposite the main spring.

FIG. 15A shows the actuator with its components in standby mode before actuation. In this mode main spring 102 is in its low temperature martensite crystal phase with a strength which is sufficiently low to enable the bias spring to drive against and hold the main spring in its standby mode. FIG. 15B shows the spring after actuation by being heated by a suitable heater (not shown) above the SMA s phase transition temperature. The SMA then reverts to its austenite phase so that the main spring elongates to its memory shape and thereby forcefully acts against and moves the plunger out while also compressing the bias spring.

Embodiment Providing Collapsible Tube

FIGS. 16A, 16B and 16C show an embodiment comprising a collapsible tube 112, such as for use in various medical applications including stents. The tube is shown for use as an intravascular medical device that has a catheter 114 which carries the tube to the desired place in a human body. The tube is comprised of a cross mesh or web of strands that are formed of a hyperelastic SMA. The cross mesh allows the tube to be easily deformed and collapsed into a size which is sufficiently small to fit within the catheter, as shown in FIG. 16A. Upon being released from the constraining catheter the mesh begins to expand as the strands deform out toward their memory shapes, as at 112 in FIG. 16B. FIG. 16C shows the mesh after emerging fully expanded from the end of the catheter as at 112 upon placement in the patient's vasculature.

The hyperelastic properties of the mesh strands enable the tube to be collapsed to a much smaller size as compared to prior art catheters, such as those employing superelastic TiNi SMA or other materials.

Embodiment Providing Solid Hinge

FIGS. 17A and 17B show an embodiment comprising a solid hinge 120 for pivotally moving elements with respect to one another. The term "solid hinge" means that it has no separate elements or parts that move with respect to one another. The hinge 120 is formed of a hyperelastic SMA. One example of the solid hinge's use is as shown in the figures for pivoting a deployable 122 (only a part of which is shown) held on a spacecraft structure 124. FIG. 17A shows the hinge in a bent shape with the deployable stowed. FIG. 17B shows the hinge bent to a flat shape after the deployable is pivoted out into its deployed position.

The hyperelastic properties of the solid hinge enable it to bend through a wider arc of travel, shown as 180 degrees, than would be possible were it to be made of superelastic SMA such as TiNi or other high strength materials. The hinge has no separate moving parts as in a piano type hinge. This results in low maintenance requirements and greater operating reliability. This is important in deep space flights where the deployable must be held by the hinge in stowed position for many years and then be depended on to properly operate when required.

The solid hinge's hyperelastic properties also enable it to bend back and forth indefinitely without losing its recoverability. The hyperelastic properties also enable the hinge to have a robust thickness, which is sufficient to provide strength for holding heavy loads while the hinge still can easily bend, These requirements of thickness/strength with ease of bending cannot be achieved by solid hinges made of other metals, metal alloys or polymer materials.

The invention claimed is:

1. A guidewire device for use in medical procedures within a body of a human or other animal, the device comprising:

an elongate guidewire body formed of a single-crystal hyperelastic alloy of copper, aluminum, and a metal selected from the group consisting of Ni, Fe, Co, and Mn having a crystalline phase change transition temperature that is below body temperature, having an austenite crystalline phase at temperatures above the phase change transition temperature and a martensite crystalline phase at temperatures below the phase change transition temperature, so that the elongate body is deformable at a constant force at recoverable strain of at least 9% at body temperature, with a very narrow loading-unloading hysteresis, a recovery which is completely repeatable and complete and a very low yield strength when martensitic, wherein the device is sized for insertion into the body and has an exposed outer surface of single-crystal alloy that is substantially free of micro- or nano-crystals, further wherein the guidewire comprises one portion having a given diameter and an other portion, the other portion having a diameter that is less than the given diameter sufficient to enable the other portion responsive to a given stress to flex through a greater degree than when the one portion is flexed responsive to the given stress.

2. A device as in claim 1 in which the hyperelastic material is single crystal of CuAlNi alloy.

3. A device as in claim 1 in which the hyperelastic material is CuAlNi alloy and its crystallographic direction <100> of the crystal is aligned with the longitudinal axis of the guidewire.

4. A device as in claim 1 in which the components of the alloy are sufficiently proportioned to provide properties of flexibility and torqueability enabling optimum movement of the guidewire through the body.

5. A device as in claim 1 and further comprising a biocompatible coating formed about the guidewire, the coating being comprised of a material selected from the group consisting of gold, a biocompatible plastic, and a biocompatible polymer.

6. A device as in claim 1 in which the guidewire has a non-elastic region comprised of a hyperelastic material having a phase change transition temperature greater than the body temperature whereby the non-elastic region, when in the body, is in a martensite phase and has malleable properties.

7. A device as in claim 1 in which the device further comprises a catheter having a hollow sleeve, and the guidewire is fitted for axial movement within the sleeve.

8. The device of claim 1, wherein the guidewire has a thickness between about 0.012 and 0.039 inches and length between about 42 and 100 inches.

9. A guidewire device for use in medical procedures within a body of a human or other animal, the device comprising:

an elongate guidewire body formed of a single-crystal hyperelastic alloy of copper, aluminum, and a metal selected from the group consisting of Ni, Fe, Co, and Mn having a crystalline phase change transition temperature that is below body temperature, having an austenite crystalline phase at temperatures above the phase change transition temperature and a martensite crystalline phase at temperatures below the phase change transition temperature, so that the elongate body is deformable at a constant force at recoverable strain of at least 9% at body temperature, with a very narrow loading-unloading hysteresis, a recovery which is completely repeatable and complete and a very low yield strength when martensitic, wherein the device is sized for insertion into the body and has an exposed outer surface of single-crystal alloy that is substantially free of micro- or nano-crystals;

further wherein the guidewire comprises one portion having a given diameter and an other portion, the other portion having a composition different from the first portion sufficient to enable the other portion responsive to a given stress to flex through a greater degree than when the one portion is flexed responsive to the given stress.

10. A guidewire device for use in medical procedures within a body of a human or other animal, the device comprising:

an elongate guidewire body formed of a single-crystal hyperelastic alloy of copper, aluminum, and a metal selected from the group consisting of Ni, Fe, Co, and Mn having a crystalline phase change transition temperature that is below body temperature, having an austenite crystalline phase at temperatures above the phase change transition temperature and a martensite crystalline phase at temperatures below the phase change transition temperature, so that the elongate body is deformable at a constant force at recoverable strain of at least 9% at body temperature, with a very narrow loading-unloading hysteresis, a recovery which is completely repeatable and complete and a very low yield strength when martensitic, wherein the device is sized for insertion into the body and has an exposed outer surface of single-crystal alloy that is substantially free of micro- or nano-crystals;

further wherein the guidewire comprises a first region having a transition temperature below 37 degrees C. and a second region having a transition temperature above 37 degrees C.

11. The device of claim 10, wherein the second region comprises a tip region.

* * * * *

UNITED STATES PATENT AND TRADEMARK OFFICE
CERTIFICATE OF CORRECTION

PATENT NO.       : 7,632,361 B2
APPLICATION NO.  : 11/041185
DATED            : December 15, 2009
INVENTOR(S)      : Johnson et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 758 days.

Signed and Sealed this

Second Day of November, 2010

David J. Kappos
*Director of the United States Patent and Trademark Office*